(12) United States Patent
Kaib et al.

(10) Patent No.: US 10,994,125 B2
(45) Date of Patent: May 4, 2021

(54) SYSTEMS AND METHODS FOR CONDUCTIVE GEL DEPLOYMENT

(71) Applicant: ZOLL MEDICAL CORPORATION, Chelmsford, MA (US)

(72) Inventors: Thomas E. Kaib, Irwin, PA (US); Gary A. Freeman, Waltham, MA (US); Phillip Hier Amsler, Oakmont, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 51 days.

(21) Appl. No.: 16/382,656

(22) Filed: Apr. 12, 2019

(65) Prior Publication Data

US 2019/0232045 A1    Aug. 1, 2019

Related U.S. Application Data

(63) Continuation of application No. 15/826,892, filed on Nov. 30, 2017, now Pat. No. 10,300,266, which is a continuation of application No. 15/072,590, filed on Mar. 17, 2016, now Pat. No. 9,861,806.

(60) Provisional application No. 62/135,495, filed on Mar. 19, 2015.

(51) Int. Cl.
*A61N 1/04* (2006.01)

(52) U.S. Cl.
CPC .......... *A61N 1/046* (2013.01); *A61N 1/0484* (2013.01); *A61N 1/0492* (2013.01)

(58) Field of Classification Search
None
See application file for complete search history.

(56) References Cited

U.S. PATENT DOCUMENTS

| 4,464,412 A | 8/1984 | Washburn |
| 4,731,926 A * | 3/1988 | Sibalis ............... A61N 1/044 29/877 |
| 5,450,845 A | 9/1995 | Axelgaard |
| 6,526,303 B1 | 2/2003 | Scampini |
| 8,725,669 B1 | 5/2014 | Fu |

(Continued)

FOREIGN PATENT DOCUMENTS

| EP | 1627605 A2 | 2/2006 |
| EP | 2351597 A1 | 8/2011 |
| KR | 20150017931 A | 2/2015 |

OTHER PUBLICATIONS

Extended European Search Report from corresponding European Application No. 16765715.4 dated Aug. 7, 2018.

(Continued)

*Primary Examiner* — Brian T Gedeon
(74) *Attorney, Agent, or Firm* — Lando & Anastasi, LLP

(57) ABSTRACT

A therapy electrode system comprises a garment configured to be worn about a torso of a patient, a therapy electrode disposed in the garment and configured to deliver one or more electrical shocks to a body of the patient, a replaceable gel cartridge disposed on the therapy electrode and configured to release a conductive gel onto the patient's skin at an interface between the therapy electrode and the patient's skin prior to the delivery of the one or more electrical shocks to the body of the patient at the interface between the therapy electrode and the patient's skin, and a fluid pump in fluid communication with the replaceable gel cartridge.

20 Claims, 22 Drawing Sheets

(56) References Cited

U.S. PATENT DOCUMENTS

| | | |
|---|---|---|
| 8,858,474 B2 | 10/2014 | Olson et al. |
| 9,132,267 B2 | 9/2015 | Kaib |
| 9,433,781 B2 | 9/2016 | Eckhous et al. |
| 9,511,239 B2 | 12/2016 | Prew et al. |
| 2007/0106170 A1 | 5/2007 | Dunseath et al. |
| 2007/0299325 A1 | 12/2007 | Farrell et al. |
| 2012/0150008 A1 | 6/2012 | Kalb et al. |
| 2015/0005588 A1 | 1/2015 | Herken et al. |
| 2017/0056682 A1 | 3/2017 | Kumar et al. |

OTHER PUBLICATIONS

International Search Report and Written Opinion from corresponding International Application No. PCT/US2016/022768 dated Aug. 4, 2016.

* cited by examiner

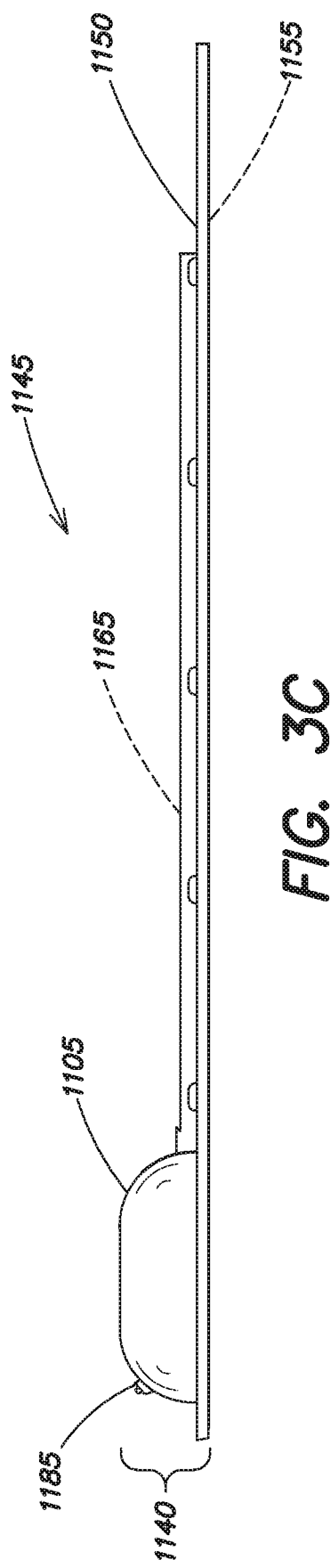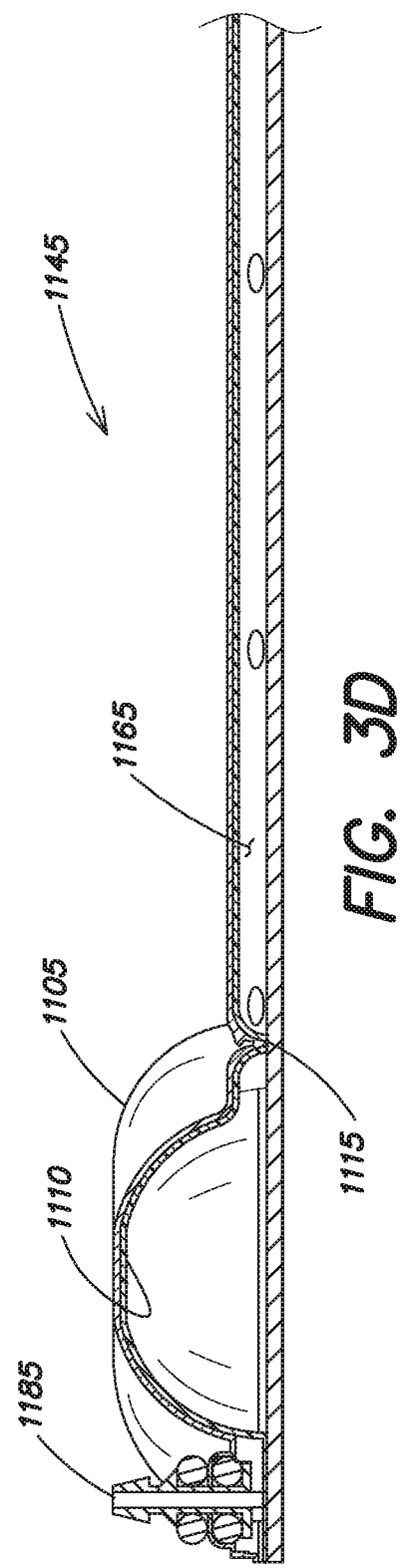

SYSTEMS AND METHODS FOR CONDUCTIVE GEL DEPLOYMENT

RELATED APPLICATIONS

The present application claims priority under 35 U.S.C. § 120 as a continuation of U.S. patent application Ser. No. 15/826,892, filed Nov. 30, 2017, titled "SYSTEMS AND METHODS FOR CONDUCTIVE GEL DEPLOYMENT," which in turn claims priority under 35 U.S.C. § 120 as a continuation of U.S. patent application Ser. No. 15/072,590, filed Mar. 17, 2016, titled "SYSTEMS AND METHODS FOR CONDUCTIVE GEL DEPLOYMENT," now U.S. Pat. No. 9,861,806, which in turn claims priority under 35 U.S.C. § 119(e) to U.S. Provisional Patent Application Ser. No. 62/135,495, filed Mar. 19, 2015, titled SYSTEMS AND METHODS FOR CONDUCTIVE GEL DEPLOYMENT. Each of these applications is hereby incorporated herein by reference in its entirety for all purposes.

FIELD

Aspects and embodiments disclosed herein relate generally to medical devices.

BACKGROUND

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

SUMMARY

In accordance with an aspect disclosed herein there is provided an electrode system. The electrode system comprises a gel deployment receptacle configured to release a conductive gel onto a body of a subject and a fluid pump in fluid communication with the gel deployment receptacle.

In some embodiments, the electrode system is capable of delivering a defibrillation current. The electrode system may be disposed within a wearable defibrillator device. The conductive gel may be capable of conducting a defibrillation current.

In some embodiments, the fluid pump receives a fluid at a first pressure and outputs the fluid at a second pressure higher than the first pressure. The fluid pump may be an air pump. The second pressure may be between about 10 psig and about 20 psig.

In some embodiments, the gel deployment receptacle comprises a shell defining a gel chamber housing a conductive gel, a fluid inlet in fluid communication with the gel chamber, and a plurality of apertures in fluid communication with the gel chamber.

In some embodiments, the gel chamber is defined on a first side of the shell. The plurality of apertures may include a plurality of shell apertures defined in a second side of the shell.

In some embodiments, the electrode system further comprises a gel conduit in fluid communication with the gel chamber and the plurality of shell apertures.

In some embodiments, the conductive gel is housed within a bladder disposed within the gel chamber.

In some embodiments, the fluid inlet is in fluid communication with an internal volume of the gel chamber and an external surface of the bladder.

In some embodiments, the gel conduit is in fluid communication with the bladder.

In some embodiments, the electrode system further comprises a seal disposed at an opening in the bladder.

In some embodiments, the bladder is disposed proximate a first end of the shell and the gel conduit extends from the bladder in a direction toward a second end of the shell.

In some embodiments, the electrode system further comprises a seal disposed within the gel conduit.

In some embodiments, the electrode system further comprises a seal disposed between the bladder and the plurality of shell apertures.

In some embodiments, the plurality of shell apertures comprises at least one first shell aperture disposed at a first distance from the bladder and at least one second shell aperture disposed at a second distance from the bladder, the second distance being greater than the first distance. A cross-sectional area of the at least one second shell aperture may be greater than a cross-sectional area of the at least one first shell aperture.

In some embodiments, the plurality of shell apertures comprises a first pair of shell apertures, each of the first pair of shell apertures being disposed at the first distance from the bladder and having a same cross-sectional area.

In some embodiments, the plurality of shell apertures comprises a plurality of pairs of shell apertures disposed along a length of the gel conduit, each shell aperture of a respective pair of shell apertures disposed at a same distance from the bladder and having a same cross-sectional area, each respective pair of shell apertures being disposed at a different distance from the bladder than each other pair of shell apertures. A cross-sectional area of each shell aperture of the respective pairs of shell apertures may increase with an increased distance from the bladder.

In some embodiments, the gel conduit comprises a trunk and a plurality of pairs of branches extending from the trunk, each of the plurality of pairs of branches providing fluid communication between the trunk and one of the plurality of shell apertures. Each of the branches may have a cross-sectional area approximately equal to a cross-sectional area of the shell aperture with which the branch is in fluid communication. The trunk may comprise a cross-sectional area approximately equal to a sum of the cross-sectional areas of the plurality of branches.

In some embodiments, the seal is configured to rupture responsive to a pressure of a fluid received at the fluid inlet.

In some embodiments, the electrode system is configured to dispense the conductive gel, responsive to a pressure of a fluid received at the fluid inlet, through the gel conduit and through the plurality of shell apertures.

In some embodiments, cross-sectional areas of the plurality of shell apertures vary along a length of the gel conduit.

In some embodiments, cross-sectional areas of the plurality of shell apertures vary along a length of the gel conduit to cause a flow rate of the conductive gel through each of the plurality of shell apertures to be within about 10% of another of the plurality of shell apertures. The plurality of shell apertures may be configured to distribute the conductive gel evenly over the second side of the shell. The plurality of shell apertures may be configured to distribute the conductive gel evenly over a conductive layer disposed on the second side of the shell.

In some embodiments, the fluid pump is disposed on the shell and in fluid communication with the fluid inlet.

In some embodiments, the electrode system further comprises a conductive layer disposed proximate to the second side of the shell.

In some embodiments, the electrode system further comprises a plurality of conductive layer apertures defined in the conductive layer, each respective conductive layer aperture circumscribing a respective shell aperture of the plurality of shell apertures.

In some embodiments, the electrode system further comprises a plurality of conductive layer apertures defined in the conductive layer, a cross-sectional area of each of the plurality of conductive layer apertures being greater than a corresponding cross-sectional area of each of the plurality of shell apertures.

In some embodiments, the electrode system is disposed in a garment including a monitor, the monitor in communication with at least one electrical component of the electrode system. The monitor may be in communication with the at least one electrical component of the electrode system by an inductive coupling system including a first coil disposed on the electrode system and a second coil disposed in the garment. The monitor may be in communication with the at least one electrical component of the electrode system by a capacitive coupling system including a first conductive plate or sheet disposed on the electrode system and a second conductive plate or sheet disposed in the garment. The monitor may be in communication with the at least one electrical component of the electrode system by an infrared signal communication system.

In some embodiments, the monitor is in communication with the at least one electrical component of the electrode system by conductive hook and loop fasteners. The conductive hook and loop fasteners may maintain the electrode system in a desired orientation relative to the garment.

In some embodiments, the monitor is in communication with the at least one electrical component of the electrode system by conductive snaps. The conductive snaps may maintain the electrode system in a desired orientation relative to the garment.

In some embodiments, the monitor is in communication with the at least one electrical component of the electrode system by one or more conductive magnets and associated conductive magnetic contacts. The one or more conductive magnets and associated conductive magnetic contacts may maintain the electrode system in a desired orientation relative to the garment.

In some embodiments, the electrode system further comprises a plurality of therapy electrodes each including a gel chamber and a fluid inlet in communication with the gel chamber, and a common distribution node. The fluid pump is disposed on the common distribution node and is in fluid communication with the fluid inlet of each of the plurality of therapy electrodes.

In some embodiments, the electrode system further comprises a plurality of therapy electrodes each including a gel chamber and a fluid inlet in communication with the gel chamber and a fluid pump disposed on each of the plurality of therapy electrodes and in fluid communication with the fluid inlet of the therapy electrode on which it is disposed.

In some embodiments, the electrode system further comprises a plurality of therapy electrodes including a first therapy electrode, a second therapy electrode, and a third therapy electrode, each of the plurality of therapy electrodes including a gel chamber and a fluid inlet in communication with the gel chamber, a first fluid pump disposed on a first therapy electrode and in fluid communication with the fluid inlet of the first therapy electrode, and a second fluid pump disposed on the second therapy electrode and in fluid communication with the fluid inlet of the second therapy electrode and the fluid inlet of the third therapy electrode.

In some embodiments, the electrode system further comprises a plurality of therapy electrodes including a front therapy electrode having a first configuration and a rear therapy electrode having a second configuration different from the first configuration, each of the plurality of therapy electrodes including a gel chamber and a fluid inlet in communication with the gel chamber, a first fluid pump disposed on the front therapy electrode and in fluid communication with the fluid inlet of the front therapy electrode, and a second fluid pump disposed on the rear therapy electrode and in fluid communication with the fluid inlet of the rear therapy electrode.

In some embodiments, the electrode system further comprises a plurality of therapy electrodes including a front therapy electrode having a first configuration and a rear therapy electrode having a second configuration different from the first configuration, each of the plurality of therapy electrodes including a gel chamber and a fluid inlet in communication with the gel chamber, and a common distribution node. The fluid pump is disposed on the common distribution node and is in fluid communication with the fluid inlet of both the front therapy electrode and the rear therapy electrode.

In some embodiments, the electrode system further comprises a plurality of therapy electrodes including a first therapy electrode, a second therapy electrode, and a third therapy electrode, and a monitor configured to monitor a physiological parameter of a subject utilizing the therapy electrode system. The fluid pump is disposed on the monitor and is in fluid communication with each therapy electrode of the plurality of therapy electrodes through the common distribution node.

In some embodiments, the electrode system further comprises a plurality of therapy electrodes including a front therapy electrode having a first configuration and a rear therapy electrode having a second configuration different from the first configuration, and a monitor configured to monitor a physiological parameter of a subject utilizing the therapy electrode system. The fluid pump is disposed on the monitor and is in fluid communication with the front therapy electrode and the rear therapy electrode through the common distribution node.

In accordance with another aspect disclosed herein there is provided an electrode system. The electrode system comprises a plurality of therapy electrodes. Each of the plurality of therapy electrodes includes a shell defining a gel chamber on a first side of the shell, a bladder disposed within the gel chamber and housing a conductive gel, a fluid inlet in fluid communication with an internal volume of the gel chamber and an external surface of the bladder, a plurality of shell apertures defined in a second side of the shell, and a gel conduit in fluid communication with the bladder and the plurality of shell apertures. The electrode system further comprises a common distribution node. Each of the plurality of therapy electrodes is at least one of fluidly connected to the common distribution node and electrically connected to the common distribution node.

In some embodiments, the electrode system further comprises a fluid pressure source disposed on the common distribution node, the fluid pressure source in fluid communication with the fluid inlet of each of the plurality of therapy electrodes.

In some embodiments, the electrode system further comprises a fluid pressure source disposed on each of the plurality of therapy electrodes and in fluid communication with the fluid inlet of the therapy electrode on which it is disposed.

In some embodiments, the plurality of therapy electrodes comprises three therapy electrodes including a first therapy electrode, a second therapy electrode, and a third therapy electrode, and the therapy electrode system further comprises a first fluid pressure source disposed on the first therapy electrode and in fluid communication with the fluid inlet of the first therapy electrode, and a second fluid pressure source disposed on the second therapy electrode and in fluid communication with the fluid inlet of the second therapy electrode and the fluid inlet of the third therapy electrode.

In some embodiments, the plurality of therapy electrodes comprises a front therapy electrode having a first configuration and a rear therapy electrode having a second configuration different from the first configuration, and the therapy electrode system further comprises a first fluid pressure source disposed on the front therapy electrode and in fluid communication with the fluid inlet of the front therapy electrode, and a second fluid pressure source disposed on the rear therapy electrode and in fluid communication with the fluid inlet of the rear therapy electrode.

In some embodiments, the plurality of therapy electrodes comprises a front therapy electrode having a first configuration and a rear therapy electrode having a second configuration different from the first configuration, and the therapy electrode system further comprises a fluid pressure source disposed on the common distribution node, the fluid pressure source in fluid communication with the fluid inlet of both the front therapy electrode and the rear therapy electrode.

In some embodiments, the plurality of therapy electrodes includes a first therapy electrode, a second therapy electrode, and a third therapy electrode, and the therapy electrode system further comprises a monitor configured to monitor a physiological parameter of a subject utilizing the therapy electrode system and a fluid pressure source disposed on the monitor and in fluid communication with the three therapy electrodes through the common distribution node.

In some embodiments, the plurality of therapy electrodes comprises a front therapy electrode having a first configuration and a rear therapy electrode having a second configuration different from the first configuration, and the therapy electrode system further comprises a monitor configured to monitor a physiological parameter of a subject utilizing the therapy electrode system and a fluid pressure source disposed on the monitor and in fluid communication with the front therapy electrode and the rear therapy electrode through the common distribution node.

In accordance with another aspect disclosed herein, there is provided a wearable monitoring device. The wearable monitoring device comprises a monitor configured to monitor a physiological parameter of a subject utilizing the wearable monitoring device, a gel chamber included in the monitor, a bladder disposed within the gel chamber and housing a conductive gel, a fluid pressure source in fluid communication with an internal volume of the gel chamber and an external surface of the bladder, and a plurality of therapy electrodes. Each of the plurality of therapy electrodes includes an electrode shell, a plurality of shell apertures defined in a side of the shell, and a gel conduit in fluid communication with the bladder and the plurality of shell apertures. The wearable monitoring device further comprises a common distribution node, each of the plurality of therapy electrodes being at least one of fluidly connected to the common distribution node and electrically connected to the common distribution node.

In some embodiments, the fluid pressure source is disposed in the monitor. The plurality of therapy electrodes may include a first therapy electrode, a second therapy electrode, and a third therapy electrode. The fluid pressure source may be in fluid communication with the three therapy electrodes through the common distribution node. The plurality of therapy electrodes may include a front therapy electrode having a first configuration and a rear therapy electrode having a second configuration different from the first configuration. The fluid pressure source may be in fluid communication with the fluid conduit of both the front therapy electrode and the rear therapy electrode.

In accordance with another aspect, there is provided an electrode system. The electrode system comprises a shell defining a gel chamber housing a conductive gel, a fluid inlet in fluid communication with the gel chamber, and a plurality of apertures in fluid communication with the gel chamber.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3C is an elevational side view of the receptacle of FIG. 3A;

FIG. 3D is a cross-sectional view of a portion of the receptacle of FIG. 3A;

DETAILED DESCRIPTION

Figure 1:
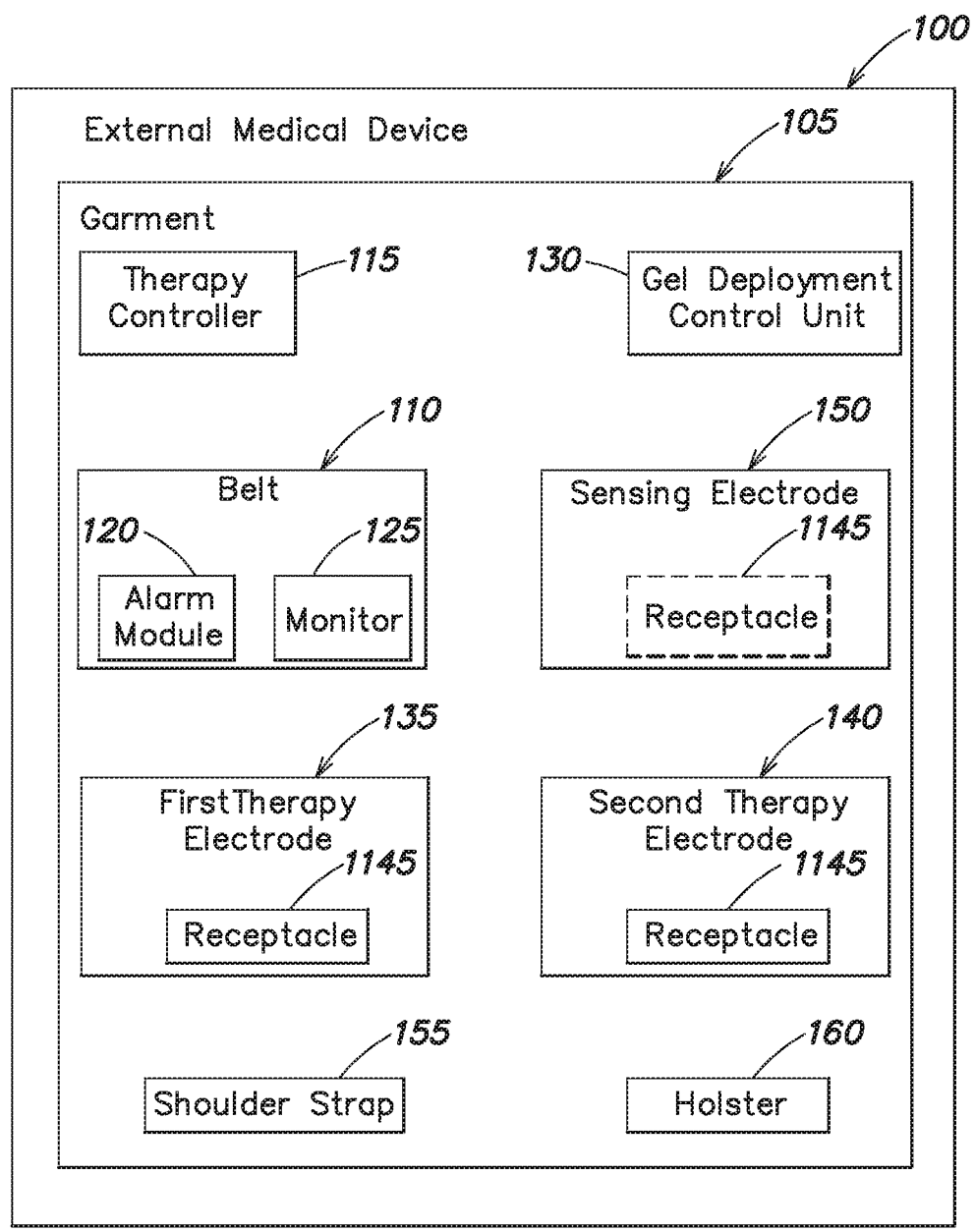
FIG. 1 is a schematic diagram depicting an external medical device, such as a wearable therapeutic device, in accordance with an embodiment.

Aspects and embodiments described herein are not limited in their application to the details of construction and the arrangement of components set forth in the description or illustrated in the drawings. Aspects and embodiments disclosed herein are capable of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter, equivalents thereof, and additional items, as well as alternate embodiments consisting of the items listed thereafter exclusively.

Various aspects and embodiments are directed to systems and methods for deploying a conductive gel in an external medical device. For example, such an external medical device can be an ambulatory monitoring and/or treatment device such as a wearable therapeutic device. The wearable therapeutic device can include monitoring electrodes, a therapy controller and a plurality of therapy electrodes configured to deliver electrical therapy, such as one or more defibrillation shocks or pacing pulses to a subject. For example, the external medical device may be a wearable therapeutic device such as the LifeVest® wearable cardioverter defibrillator available from ZOLL Medical Corporation of Chelmsford, Mass. In other examples, the external medical device may be a stationary device that may be utilized, for example, in a hospital setting or an automated external defibrillator (AED).

The external medical device can be configured to house at least one receptacle including conductive gel. For example, the receptacle may be housed within at least one therapy electrode in the device. In an example, the receptacle may be removable or separable from the at least one therapy electrode for replacement by a patient or service personnel. Prior to delivering an electric shock, a gel deployment control unit can direct the at least one receptacle to release the conductive gel onto the plurality of therapy electrodes, lowering an impedance between the subject's skin and the therapy electrodes. In some examples described herein, the control unit can actuate a fluid pump that in turn can cause the at least one receptacle to release the conductive gel. After the conductive gel is deployed, the therapy controller can administer an electric shock or pacing pulse to the subject via the therapy electrodes and conductive gel. The therapy electrodes can be housed in or on a garment of the external medical device.

In one example, spent receptacles can be removed from the external medical device and replaced with fresh receptacles that contain at least one dose of conductive gel. For example, the spent receptacles can be replaced when the external medical device is returned to a service center for servicing and/or refurbishing.

FIG. 1 is a schematic diagram of an external medical device 100 in accordance with an embodiment. In one embodiment, external medical device 100 includes a garment 105. Garment 105 may be similar to the garment disclosed in commonly owned U.S. Pat. No. 9,008,801, titled "WEARABLE THERAPEUTIC DEVICE," which issued on Apr. 14, 2015, the disclosure of which is incorporated herein by reference in its entirety, or in commonly owned U.S. patent application Ser. No. 13/460,250, titled "PATENT-WORN ENERGY DELIVERY APPARATUS AND TECHNIQUES FOR SIZING SAME," filed on Apr. 30, 2012, the disclosure of which is incorporated herein by reference in its entirety.

In one embodiment garment 105 includes a belt 110. Belt 110 may be worn about a subject's waist, at a higher location about the subject's chest, or at other locations between the subject's waist and shoulders. Components of external medical device 100 can be worn under, over, or partially under and partially over a subject's clothes.

Figure 2:
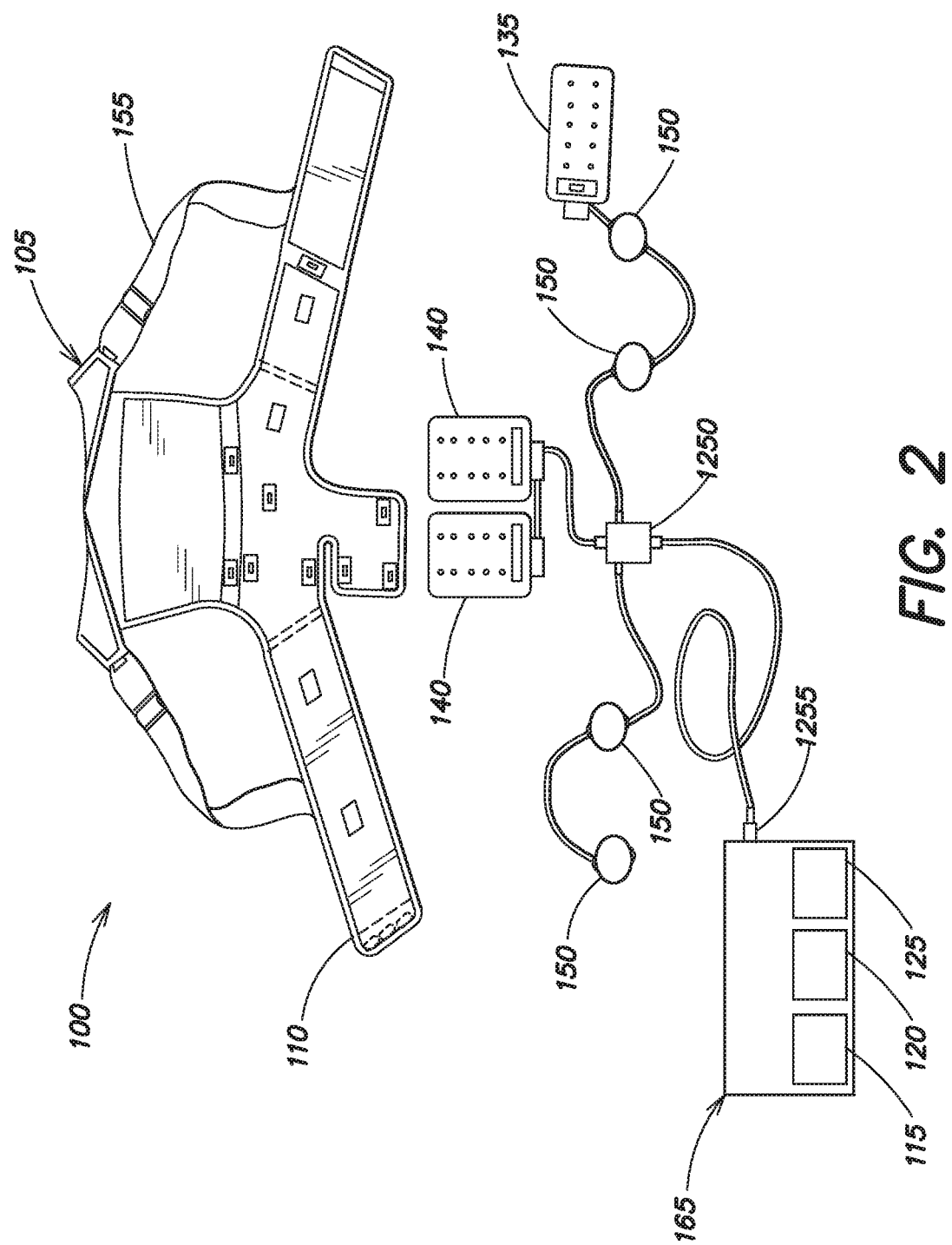
FIG. 2 is an illustration of a wearable therapeutic device, e.g., a wearable defibrillator, in accordance with an embodiment.

The external medical device 100 includes the following elements: garment 105, including belt 110, therapy controller 115, alarm module 120, monitor 125, gel deployment control unit 130, first therapy electrode 135, second therapy electrode 140, receptacles 1145 in or proximate each of the therapy electrodes 135, 140, one or more cardiac sensing electrodes 150, which may each also include or be disposed proximate a receptacle 1145 (as shown in dotted lines), shoulder strap 155, and holster 160. First therapy electrode 135 may include at least one front therapy electrode and second therapy electrode 140 may include at least one rear therapy electrode. In one embodiment, at least one of therapy controller 115, alarm module 120, monitor 125, gel deployment control unit 130, at least one front therapy electrode 135, at least one rear therapy electrode 140, receptacle 1145, at least one sensing electrode 150, shoulder strap 155, and/or holster 160 can be included in or attached to belt 110. In an implementation, the at least one rear therapy electrode 140 can further include at least two rear therapy electrodes as shown in FIG. 2. In some examples, at least one of alarm module 120 and monitor 125 can be fitted to open or closed pockets of belt 110 or garment 105 or otherwise attached to belt 110 or garment 105 via buttons, hook and loop fasteners, straps, snaps, magnets, or sleeves, or another attachment mechanism that forms part of belt 110 or garment 105. These elements may also be integrated into belt 110 or garment 105, and as such, may be a permanent part of belt 110 or garment 105. In some examples, the alarm module 120 can be integrated into and a part of the monitor 125. External medical device 100 may include the above mentioned elements, as well as additional elements.

FIG. 2 is an illustration of an embodiment of the external medical device 100 with the electrode components shown removed from the garment. As depicted in FIG. 2, the therapy controller 115, the alarm module 120, and the monitor 125 can be integrated into a portable medical device control unit 165 that can be attached to the garment 105.

Therapy controller 115 is included in garment 105. Therapy controller 115 can be attached to shoulder strap 155, or disposed in holster 160. Holster 160 may attach to or be part of garment 105, shoulder strap 155, or belt 110. In some implementations, therapy controller 115, alarm module 120, and monitor 125 are combined into a single medical device control unit 165 that may be attached to or carried in the garment 105. Therapy controller 115 is electrically coupled to first therapy electrode 135 and second therapy electrode 140. In some embodiments, therapy controller 115 is also electrically coupled to one or more sensing electrodes 150. Each of electrodes 135, 140 has an associated receptacle 1145. In one embodiment, therapy controller 115 may include the defibrillator described in commonly owned U.S. Pat. No. 6,280,461, titled "PATENT-WORN ENERGY DELIVERY APPARATUS," which issued on Aug. 28, 2001, and which is incorporated by reference herein in its entirety.

Monitor 125 or control circuitry of therapy controller 115 monitors a subject's condition. For example, the one or more sensing electrodes 150 can sense electrical activity of the subject's heart signals. When an arrhythmic event is detected, alarm module 120 sounds a warning that the subject wearing external medical device 100 is in danger of, or is experiencing, a heart attack, cardiac arrest, or other form of cardiac distress. This warning may be audio, visual, haptic (e.g., vibrating alarm module 120) or combinations thereof. The signals sensed by the one or more sensing electrodes 150 can be displayed as electrocardiograph signals on monitor 125. This and other information can be stored in memory units associated with monitor 125 or therapy controller 115 for analysis by a doctor, rescuer, or health care provider.

Alarm module 120 may provide an alarm that indicates that the subject will receive a defibrillation shock from therapy controller 115 delivered by the first therapy electrode 135 and second therapy electrode 140 unless the subject wearing external medical device 100 takes some action to prevent therapy controller 115 from applying the shock. For example, alarm module 120 or monitor 125 may include a user interface having at least one button or touch screen. In this example, the subject can depress the at least one button to indicate that the subject is conscious. In this example, the defibrillation shock will not be applied while the subject depresses the at least one button for a sufficient amount of time, or if control logic of therapy controller 115 determines that the electrical heart activity of the subject (as detected by sensing electrode 150) has returned to normal. Continuing with this example, if the subject loses consciousness, the subject will release the at least one button and therapy controller 115 will apply a defibrillation shock via the first therapy electrode 135 and second therapy electrode 140.

First therapy electrode 135 includes at least one front therapy electrode positioned in garment 105 in front (e.g., anterior or about the chest) of the subject, and second therapy electrode 140 includes at least one therapy electrode positioned in garment 105 at the rear (e.g. posterior or about the back) of the subject. Other anterior, posterior, and lateral positioning with respect to the subject when the subject is wearing garment 105 is possible. For example, first therapy electrode 135 and second therapy electrode 140 may both be in an anterior position with respect to the subject. In one embodiment, multiple therapy electrodes are disposed in an anterior position. Multiple therapy electrodes may also be disposed in any position, e.g., anterior, posterior, or lateral.

In one embodiment, first therapy electrode 135 and second therapy electrode 140 may be permanent components of external medical device 100. Electrodes 135 and 140 can be housed anywhere in garment 105. For example, first therapy electrode 135 can be integral to garment 105 and disposed proximate to the subject's chest or abdomen when the subject is wearing external medical device 100. Second therapy electrode 135 can be integral to garment 105 and disposed proximate to the subject's back when the subject is wearing external medical device 100. In one embodiment, when a shock is applied, first therapy electrode 135, second therapy electrode 140, the subject's body, and therapy controller 115 form at least part of a current path for the shock. In some embodiments, for example, as illustrated in FIG. 2, electrodes 135, 140, and 150 may be coupled to a common distribution node 1250, described in more detail below. An electrical connector 1255 may electrically connect the common distribution node 1250 to a monitor 125.

Configuration of Conductive Gel Receptacles

Figure 3A:
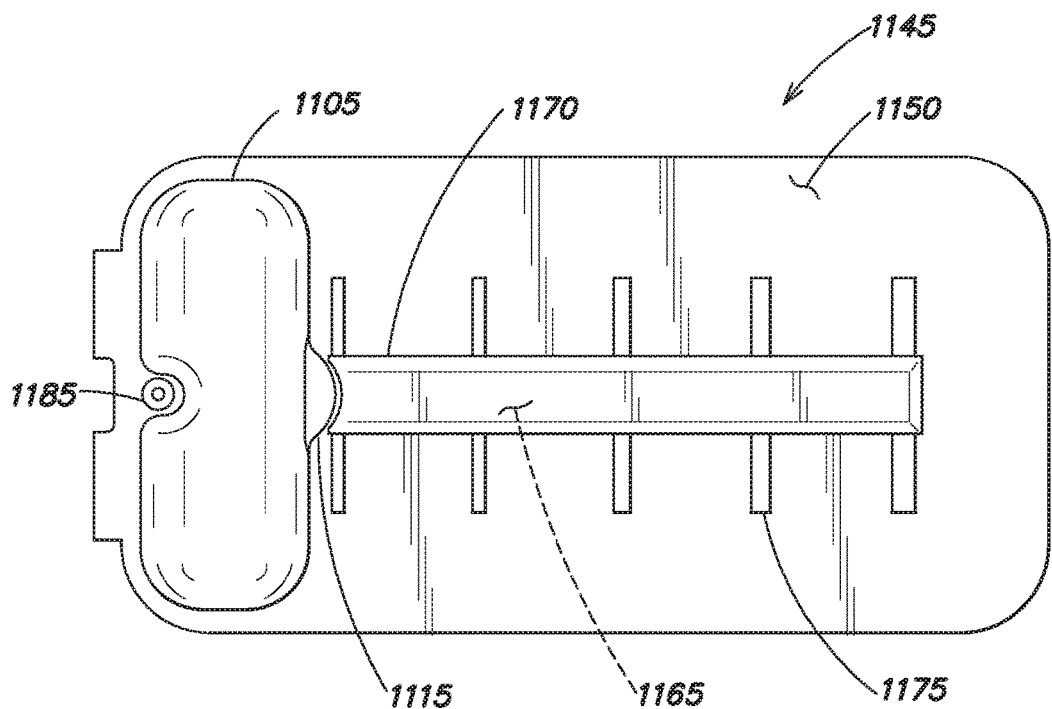
FIG. 3A is a plan view of a receptacle for an external medical device in accordance with an embodiment.
Figure 3B:
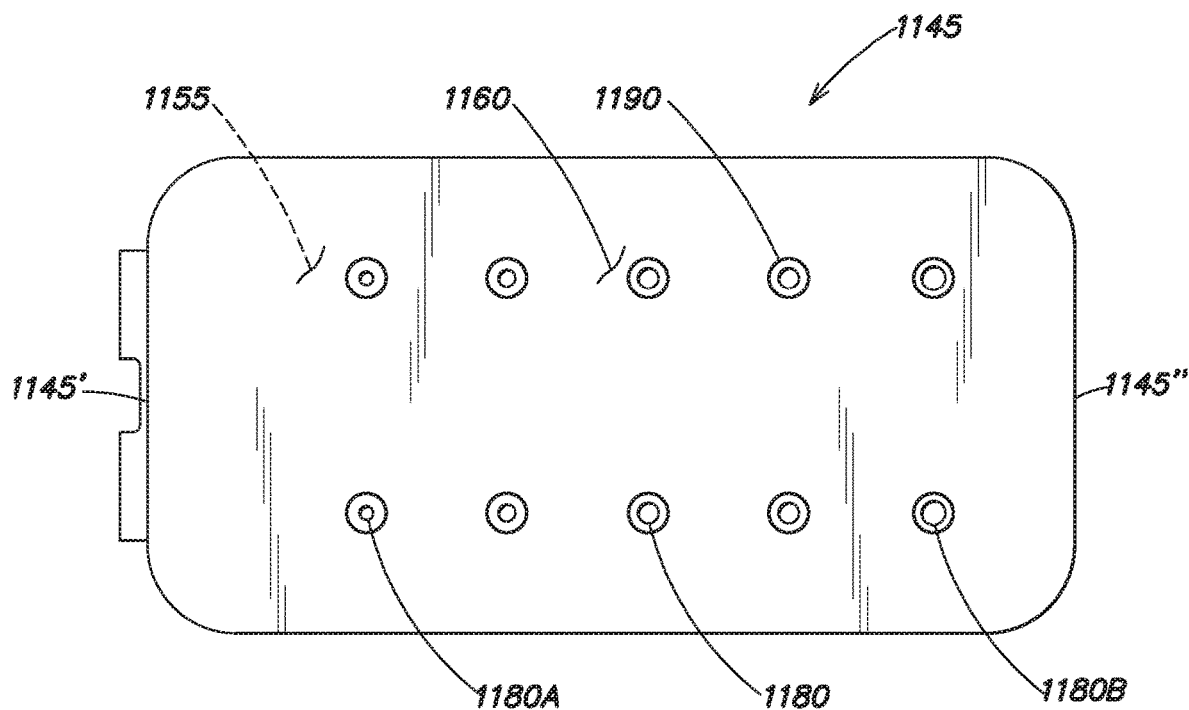
FIG. 3B is a view of the underside of the receptacle of FIG. 3A.

An example receptacle 1145 that can be used with embodiments of the external medical device 100 is shown in FIGS. 3A-D. A person of ordinary skill in the art will appreciate that the example receptacle 1145 shown in FIGS. 3A-D is for illustration only and does not limit the claims. For example, receptacle 1145 can include a shell 1140 (see FIG. 3C) having an upper portion defining an upper surface 1150 of the receptacle 1145 and a lower portion defining a lower surface 1155 of the receptacle 1145. In some embodiments, such as illustrated in FIG. 3B, the lower surface 1155 can be at least partially covered with a conductive layer 1160 to form a therapy electrode (e.g., for use as one of therapy electrodes 135, 140). The conductive layer 1160 can be formed from, for example, a layer of metal adhered to the lower surface 1155. The layer of metal may include, for example, tin, silver, stainless steel, or other metals, metal oxides, or mixtures thereof. In some embodiments, the layer of metal may be replaced or supplemented with a non-metallic conductive material, for example, a conductive polymer, carbon fiber, a material including conductive particles dispersed in it, or any other material that is electrically conductive and that may also be biocompatible and/or corrosion resistant.

In some examples, the receptacle 1145 and conductive layer 1160 can form a monitoring/sensing electrode for detecting a signal (e.g., a cardiac signal) from the patient. In some examples, the receptacle 1145 can include one or more conductive layers and/or sensors for performing both monitoring/sensing a patient signal and providing a therapeutic treatment.

One or more electrical connectors (not shown) can electrically connect the conductive layer 1160 to the therapy controller 115 to enable it to function as one of the therapy electrodes 135, 140 of embodiments of the external medical device disclosed herein. In other embodiments, the receptacle 1145 may not include conductive layer 1160 and the receptacle 1145 may be configured to dispense conductive gel onto or proximate to a therapy electrode that is formed separately from the receptacle 1145. In some embodiments, the receptacle 1145 may be removably attached to the therapy electrode 135, 140 (e.g., by being at least removably attached to the conductive layer 1160).

In one example, a gel chamber 1105 can be defined in an upper portion of the shell of the receptacle 1145 for containing the conductive gel (not shown). In use, when a defibrillation shock is to be applied to a subject wearing a wearable therapeutic device including the receptacle 1145, an external pressure can be applied to the conductive gel through the use of an external pressure source or a pressure source device. For example, the pressure can be applied to the internal volume of the gel chamber 1105. In some implementations, the pressure source can be a fluid pump (e.g., an air pump) as described in further detail below. For example, the fluid can be physically separated from the conductive gel by a membrane such that pressure applied by the fluid on one side of the membrane can cause the conductive gel that is disposed on the other side of the membrane to be deployed.

In some implementations, the conductive gel can be contained within a bladder 1110 (see FIG. 3D) disposed within the gel chamber 1105. In some examples, the gel chamber 1105 and/or the bladder 1110 can include a mechanism for separating the gel from the rest of the delivery system (e.g., the gel conduit 1165) that can be configured to allow a flow of the gel from the gel chamber and/or bladder 1110 once a pressure threshold is reached or exceeded as described below. For example, such a mechanism can include a seal 1115. The pressure can build up in the gel chamber 1105 and can cause the seal 1115 to rupture at, for example, about 15 psig. In some examples, the seal can be configured to release the gel at any pressure value in a range of 10-20 psig. A person of ordinary skill in the art will recognize that the range of values provided herein is for illustration only and, in some examples, values above or below this range may be used. For example, the pressure range can be increased to a range of 20-30 psig and still be in accordance with the concepts described herein. Further, while seal 1115 is shown to be disposed at a location between gel chamber 1105 and a gel conduit 1165, it should be understood that seal 1115 can be placed anywhere within gel conduit 1165 on or in the receptacle 1145, for example, defined in the top portion of the receptacle 1145 as shown in FIG. 3A, and/or within the gel chamber 1105 and/or on the bladder 1110.

When seal 1115 ruptures, the conductive gel contained within bladder 1110 flows through a main trunk 1170 of the gel conduit 1165, through branches 1175 of the gel conduit 1165, and through shell apertures 1180 defined in the lower portion of the shell to provide a conductive path between a therapy electrode 135, 140 and a body of a subject wearing the external medical device 100. In some examples, the external pressure source can cause pressure to be applied for a predetermined duration to reach the threshold (e.g., 10-20 psig) necessary for causing the seal 1115 to rupture and further ensuring that substantially all or at least a significant amount of the conductive gel is deployed. In some embodiments, the pressure can be applied until all conductive gel from the gel chamber 1105 and/or bladder 1110 is dispensed through the shell apertures 1180. For example, depending on a location of the pressure source, the pressure can be applied for approximately 10 seconds (generally in a range of 2-15 seconds) before the pressure source is turned off. In some examples, a sensing circuit (as described below) can detect if a desired impedance value is reached and cause the pressure source device to be turned off responsive to the desired impedance value having been reached.

In other embodiments, some conductive gel may remain, for example, within one or more portions of the gel conduit 1165 after the receptacle 1145 is activated to dispense the conductive gel.

In some embodiments, the bladder 1110 is not included within the gel chamber 1105 and the conductive gel may be disposed in direct contact with internal surfaces of the gel chamber 1105. As such, the fluid from the fluid pump may directly contact the conductive gel. In other embodiments, the gel chamber 1105 need not be defined in the upper portion of the shell of the receptacle 1145. For example, the gel chamber 1105 may straddle the upper and lower portions of the shell. In other embodiments, the gel chamber 1105 need not even be defined on or in the shell of the receptacle 1145, but may be disposed separate from the receptacle 1145, for example, on a separate receptacle 1145 or on or in another component of the external medical device 100. In some examples, the bladder 1110 may be only partially disposed within the gel chamber 1105 (or even the receptacle 1145) and as such a portion of the bladder 1110 may be disposed external to the gel chamber 1105 (or receptacle 1145).

A source of the external pressure that is applied to bladder 1110 within gel chamber 1105 may be a gas cartridge as disclosed in commonly owned U.S. Pat. No. 8,406,842, titled "ELECTRODE WITH REDUNDANT IMPEDANCE REDUCTION," which issued on Mar. 26, 2013, and which is incorporated herein by reference in its entirety. Alternatively, the source of pressure can be a fluid pump 1200 (see FIG. 4) which may be disposed to be either part of the therapy electrode 135, 140, or to be external to the receptacle 1145, for example, disposed on or in the monitor 125 or on another portion of the belt 110 or garment 105 as described further below. For example, the fluid pump can be implemented within or in the form of a removable cartridge. After the gel is deployed, the spent cartridge can be removed and replaced with a new cartridge.

In some embodiments, the fluid pump 1200 is an air pump. The fluid pump 1200 may receive or intake a fluid, for example, air, at a first pressure and output the fluid at a second pressure higher than the first pressure by, for example, between about 10 psig (about 69 kPa gauge) and about 20 psig (about 138 kPa gauge). In some embodiments, the fluid pump 1200 may include a model KPM27H miniature air pump, or one of the other miniature air pumps available from Koge Electronics Co., Ltd. The fluid pump 1200 may have dimensions of about 2.72 in×1.46 in×1.18 in (6.9 cm×3.7 cm×3.0 cm). The fluid pump 1200 utilized in embodiments disclosed herein, however, is not limited to a KPM27H miniature air pump. Any fluid or air pressure pump capable of providing sufficient pressure to cause release of the conductive gel from a receptacle 1145 may be utilized.

The fluid pump 1200 provides pressurized fluid, for example, air to the internal volume of the gel chamber 1105 and/or to an external surface of the bladder 1110 within the gel chamber 1105 through a fluid conduit or tube fluidly connecting an output of the fluid pump 1200 with a fluid inlet 1185 disposed on the receptacle 1145, for example, on the upper portion of the receptacle 1145 as shown in FIG. 3A. In some embodiments an intermediate chamber or conduit may be provided between the fluid pump 1200 and fluid inlet 1185 and/or between the fluid inlet 1185 and the gel chamber 1105. The fluid pump 1200, in some embodiments, provides a pressure of between about 10 psig and about 15 psig to the internal volume of the gel chamber 1105 and/or external surface of the bladder 1110. As detailed above, this pressure range can be varied to be higher or lower than 10-15 psig. For instance, the range can be selected to be 15-30 psig.

In some examples, the source of external pressure (the "fluid pressure source") can be in the form of a plunger mechanism disposed within a barrel (e.g., cylindrical or any other shape), such as in a syringe. In such cases, the conductive gel can be disposed within the barrel (or tube). When the plunger is actuated, e.g., by a mechanism activated in accordance with the principles described herein, the gel can be expelled from within the barrel or tube. For example, a seal can be placed over an orifice at an open end of the tube. When the plunger is actuated, the seal can be ruptured as described herein, and the conductive gel can be released. For example, a syringe pump can be activated to release conductive gel in accordance with the concepts described herein.

In some examples, a different fluid can be disposed within the barrel to serve as a working fluid in applying pressure directly or indirectly to the conductive gel. For example, the conductive gel can be disposed within a bladder (such as bladder 1110). The working fluid can be expelled via the orifice in the syringe such that the resultant pressure is applied directly to the conductive gel or, e.g., through a wall of the bladder 1110, if the gel is disposed within the bladder 1110.

For example, the syringe pump can be implemented within or in the form of a removable cartridge. After the gel is deployed, the spent cartridge can be removed and replaced with a new cartridge.

In some implementations, the external pressure source can be a peristaltic pump. For example, such a pump can include a rotary mechanism having rollers (or "lobes") for compressing or pinching closed a flexible, circular tube inside a circular pump casing. In some examples, apart from or in addition to a circular peristaltic pump, a linear peristaltic pump can be employed for a same or similar effect.

In some examples, the fluid in the pump can be the conductive gel. In other examples, the fluid can be a working fluid which can be used to apply pressure directly or indirectly to the conductive gel in accordance with the principles described herein. For example, the peristaltic pump can be implemented within or in the form of a removable cartridge. After the gel is deployed, the spent cartridge can be removed and replaced with a new cartridge.

In some embodiments, the receptacle 1145 includes a plurality of shell apertures 1180. For example, the apertures 1180 can be sized and spatially distributed to cause the gel to be substantially evenly distributed over the area of contact of the therapy electrode with the patient's skin. An example of such sizing and spacing is shown below. It should be understood, however, that other patterns and/or distributions of shell apertures 1180 can be used to similarly result in a substantially even distribution of the conductive gel.

For example, the receptacle 1145 illustrated in FIG. 3B includes ten shell apertures 1180. More or fewer shell apertures 1180 may be provided. As shown in FIG. 3B the shell apertures 1180 may be arranged in pairs, specifically, five pairs of shell apertures 1180.

As shown, each shell aperture 1180 in a pair of shell apertures 1180 is disposed at a common distance from a first end 1145' and second end 1145" of the receptacle and from the gel chamber 1105 and/or bladder 1110. Each shell aperture 1180 in a pair of shell apertures 1180 has a common length and/or volume of gel conduit 1165 between the shell aperture 1180 and the gel chamber 1105 and/or bladder 1110.

The shell apertures 1180 are sized such that upon dispensing of the conductive gel from the receptacle 1145, a substantially same amount of conductive gel flows through each of the shell apertures 1180. For example, in some embodiments, the shell apertures 1180 are sized such that upon dispensing of the conductive gel from the receptacle 1145 a rate and/or an amount of gel dispensed through any shell aperture 1180 is between about 1% and 20%, for example, within about 10%, of a rate and/or amount of conductive gel dispensed through any other of the shell apertures 1180. To accomplish this, the shell apertures 1180 may be configured to increase in cross-sectional area or diameter with increasing distance from the gel chamber 1105 and/or bladder 1110. In some implementations, each shell aperture 1180 in a pair of shell apertures 1180 located at a same or similar distance from the gel chamber 1105 and/or bladder 1110 may have a same or similar cross-sectional area or diameter. For example, in some cases, each aperture in a pair of apertures 1180 may have a cross-sectional area that is within about 2% of a cross-sectional area of the other aperture in the pair of apertures 1180.

In a specific, non-limiting example, the shell apertures 1180A closest to the gel chamber 1105 and/or bladder 1110 have a diameter of about 0.051 inches (0.13 cm) and the shell apertures 1180B furthest from the gel chamber 1105 and/or bladder 1110 have a diameter of about 0.067 inches (0.17 cm). The branches 1175 of the gel conduit 1165 have similar or the same cross-sectional areas as the respective shell apertures 1180 at which they terminate and thus, as shown in FIG. 3A, the cross-sectional area of the branches 1175 increase with increasing distance from the gel chamber 1105 and/or bladder 1110. The main trunk 1170 of the gel conduit 1165 has a cross-sectional area about equal to the sum of the cross-sectional areas of each of the branches 1175.

In embodiments of receptacles 1145 including a conductive layer 1160, the conductive layer 1160 includes a plurality of conductive layer apertures 1190 corresponding to the shell apertures 1180. In some implementations, there may be a one-to-one correspondence between shell apertures 1180 and conductive layer apertures 1190. For example, each conductive layer aperture 1190 circumscribes a single shell aperture 1180. Each conductive layer apertures 1190 has a diameter and/or cross-sectional area greater than that of the shell aperture 1180 that it circumscribes so as not to interfere with the passage of conductive gel through the shell aperture 1180. In some embodiments, each conductive layer aperture 1190 has a similar or same diameter and/or cross-sectional area as each other conductive layer aperture 1190.

Example Alternative Gel Deployment Apparatus

In some implementations, the gel deployment apparatus can include a plurality of tubes (or a single main tube comprises a plurality of branch tubes) disposed on a flexible frame in a predetermined arrangement. For example, the one or more tubes can be arranged to carry conductive gel from a gel chamber (e.g., located in the monitor) and dispense the gel substantially evenly over a surface of the patient's skin that is in contact with a conductive surface of a therapy electrode. For example, the tubes can be configured to be distributed in the form of pairs of tubes branching out on either side of a central line of the frame (e.g., in a manner similar to the arrangement shown for FIGS. 3A-3D). For example, the plurality of tubes can comprise five or more pairs of tubes arranged to be distributed along a length of the frame. In some implementations, a cross-sectional area or a diameter of the tubes can vary in a similar manner as described above.

For example, tubes may be sized such that upon dispensing of the conductive gel, a substantially same amount of conductive gel flows through each of the tubes. For example, in some embodiments, the tubes may be sized such that upon dispensing of the conductive gel a rate and/or an amount of gel dispensed through any tube is between about 1% and 20%, for example, within about 10%, of a rate and/or amount of conductive gel dispensed through any other tube. To accomplish this, tubes may be configured to increase in cross-sectional area or diameter with increasing distance from a gel chamber. In some implementations, each tube in a pair of tubes located at a same or similar distance from a gel chamber may have a same or similar cross-sectional area or diameter. For example, in some cases, each tube in a pair of tubes may have a cross-sectional area that is within about 2% of a cross-sectional area of the other tube in the pair of tubes.

In some examples, the gel chamber in communication with the tubes (along with the tubes and the associated gel deployment circuitry) can be implemented within or in the form of a removable cartridge that is disposed within any of the monitor, distribution node, and/or one or more electrodes. In some implementations, only the gel chamber may be within the removable cartridge so that the associated gel deployment circuitry can be reused and not discarded. After the gel is deployed, the spent cartridge can be removed and replaced with a new cartridge.

Example Conductive Gel Activation Mechanisms

Figure 4:
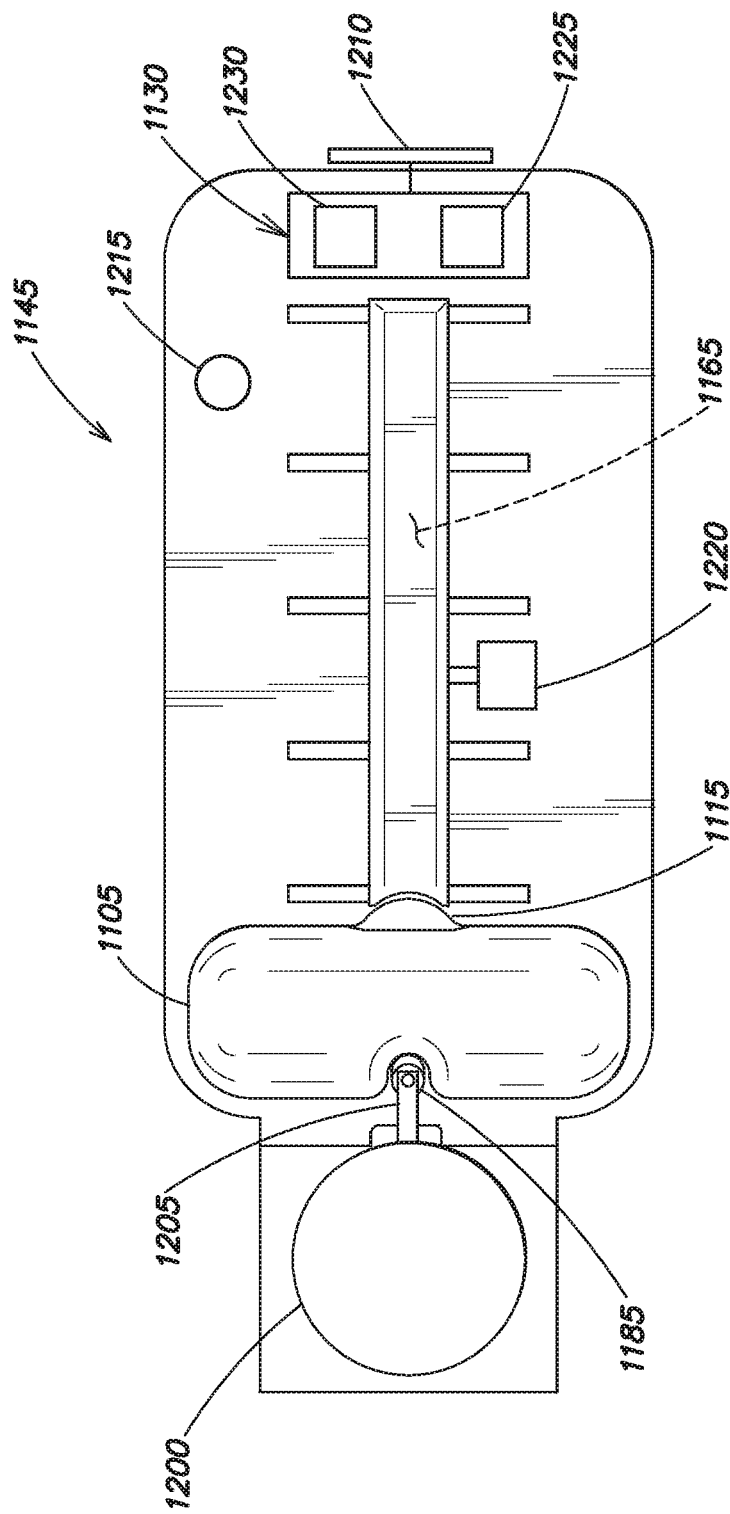
FIG. 4 is a plan view of a receptacle for an external medical device in accordance with an embodiment.

In an embodiment, for example, as illustrated in FIG. 4, a pressure source (e.g., fluid pump 1200) is incorporated on one or more of the therapy electrodes 135, 140 themselves (rather than in, e.g., the distribution node or the monitor). It should be understood that any other pressure sources and/or mechanisms described above may be used (e.g., a syringe or a peristaltic pump).

Fluid pump 1200 can be coupled to or mounted on a portion of the receptacle 1145, for example, on the upper surface 1150 of the receptacle 1145 or an extension thereof. The fluid pump 1200 may be fluidly coupled by a fluid pressure conduit 1205 to the fluid inlet 1185 or directly to the internal volume of the gel chamber 1105. In some embodiments, the fluid pump 1200 is removably coupled to the receptacle 1145 so that the fluid pump 1200 may be reused with a different receptacle 1145 upon failure of a first receptacle 1145 to which it is coupled and/or after activation of the first receptacle 1145 if the first receptacle 1145 is a single use receptacle 1145.

Receptacle 1145 can include various sensors and/or electrical and/or electronic components for causing deployment of the conductive gel and detecting the event of gel deployment, a quantity of gel deployed, and/or a measure of a change in impedance caused by the gel deployment. For example, the receptacle 1145 may include a gel deployment control unit 1130 including an activator circuit 1230. Activator circuit 1230 may receive an activation signal from, for example, therapy controller 115 or monitor 125 indicating that the receptacle 1145 should release conductive gel. Responsive to receipt of the activation signal, activator circuit 1230 may send current from, for example, a battery 1215 located on the receptacle 1145 or elsewhere on or in the external medical device 100, to the pressure source 1200 (e.g., the fluid pump) to pressurize the gel chamber 1105 and/or bladder 110, cause the seal 1115 to rupture, and cause the release of conductive gel from receptacle 1145.

In some embodiments, receptacle 1145 further includes a sensing circuit 1225. Sensing circuit 1225 may include functionality to determine and provide an indication, for example, via monitor 125, of whether the therapy electrode 135, 140 is functional, properly connected, and/or properly aligned in garment 105. For example, such a sensing circuit 1225 can be one or more orientation circuits described in commonly owned U.S. Pat. No. 9,007,216, titled "WEARABLE THERAPEUTIC DEVICE," which issued on Apr. 14, 2015, the disclosure of which is incorporated herein by reference in its entirety.

Sensing circuit 1225 may additionally or alternatively be configured to communicate with a pressure sensor 1220 disposed on receptacle 1145 or external to receptacle 1145 to make a determination as to whether portions of receptacle 1145, for example, gel conduit 1165 and/or bladder 1110 and/or gel chamber 1105 are intact. Pressure sensor 1220 may be configured to monitor the pressure in one or more portions of the receptacle 1145, for example, in the gel conduit 1165 and/or bladder 1110 and/or gel chamber 1105 to monitor for faults. For example, the gel conduit 1165 and/or bladder 1110 and/or gel chamber 1105 may be at least partially evacuated or pressurized. A rupture in the gel conduit 1165 and/or bladder 1110 and/or gel chamber 1105 may result in a pressure change in the gel conduit 1165 and/or bladder 1110 and/or gel chamber 1105 which may be sensed by the pressure sensor 1220. The pressure sensor 1220 may provide an indication of the error condition to one or more other components of the wearable therapeutic device, for example, sensing circuit 1225 and/or alarm module 120, and/or monitor 125. In some examples, the control unit 1130 can determine if a receptacle 1145 needs to be replaced, for example, if sensing circuit 1225 receives a signal from pressure sensor 1220 indicative of the conductive gel having been released or the gel conduit 1165 or bladder 1110 and/or gel chamber 1105 having been ruptured.

Figure 5:
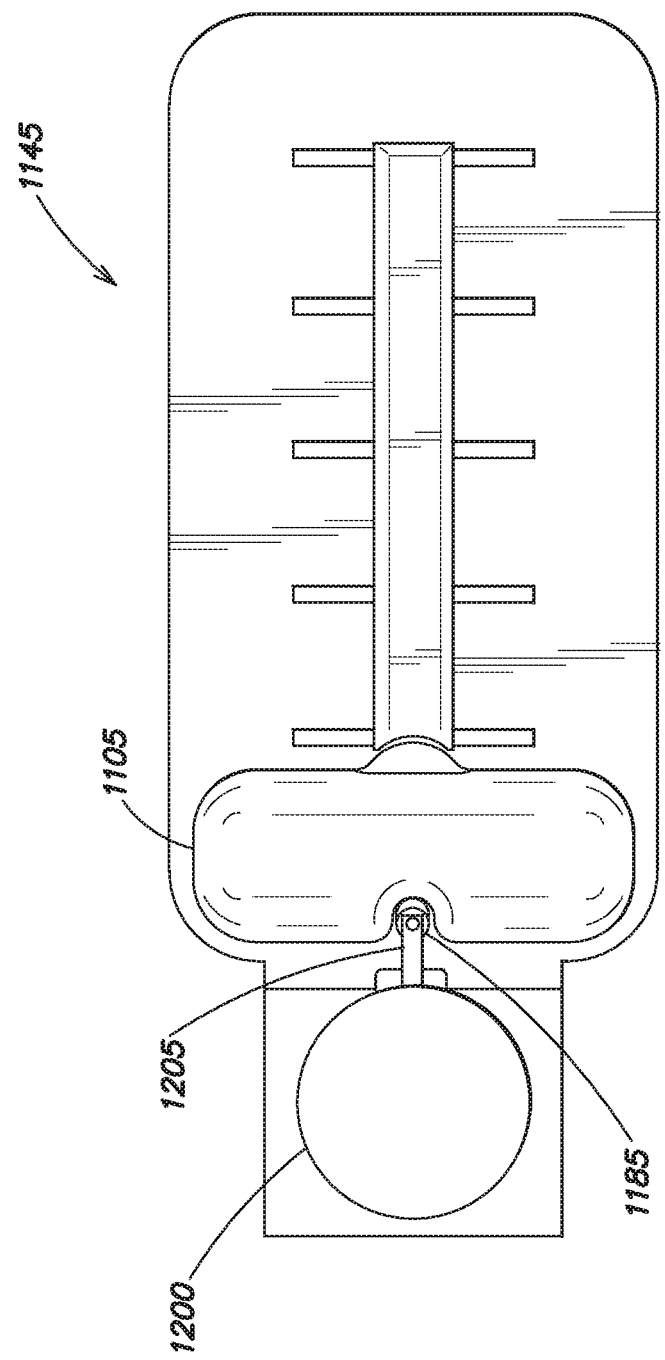
FIG. 5 is a plan view of a receptacle for an external medical device in accordance with an embodiment.

In some embodiments, one or more functions of gel deployment control unit 1130 may be alternatively be performed by a control unit 130 disposed external to receptacle 1145 in a portion of the garment 105, for example in monitor 125 or therapy controller 115. For example, as illustrated in FIG. 5, receptacle 1145 may be free of electronic components but include a pressure source (e.g., fluid pump 1200).

Embodiments of the receptacle 1145 may also include a connection port 1210. The connection port 1210 provides for communication between electrical and/or electronic components of the receptacle 1145, for example, any one or more of the control unit 1130, sensing circuit 1225, activator circuit 1230, and pressure sensor 1220 and components of the garment, for example, therapy controller 115, alarm module 120 and/or monitor 125. In some embodiments, power is provided through the connection port 1210 from an external source, for example, a battery located in a portion of the garment 105 to power components of the receptacle 1145 and/or charge the battery 1215 as needed. The connection port 1210 may include a winding of an induction coil that provides electromagnetic connection with components of the garment, for example, alarm module 120 and/or monitor 125 through a complementary winding of the induction coil disposed on or in the garment 105.

In other embodiments, the connection port 1210 may include one or more connectors, for example, one or more conductive snaps and/or conductive hook and loop fasteners and/or conductive magnets and conductive magnetic contacts having complimentary portions disposed on the receptacle 1145 and the garment 105 to form an electromechanical and/or electrical connection between receptacle 1145 and garment 105 and provide a communication pathway between one or more components of the receptacle 1145 and one or more components of the garment 105. The connector(s) may facilitate or further help ensure proper alignment of the receptacle 1145 within the garment 105. If the receptacle 1145 is not properly aligned with the garment 105, the connector(s) on the receptacle 1145 will not be able to properly couple to the complementary connector(s) in the garment 105, and an indicator of improper alignment may be provided, for example, via monitor 125. In some embodiments, alternative or additional wired or wireless means, for example, one or more RF or infrared transmitters, receivers, or transceivers having complimentary components located in the garment 105 and in the receptacle 1145 may be utilized to provide communication between one or more components of the receptacle 1145 and one or more components of the garment 105. In some embodiments, conductive plates, sheets, or films, for example, metallic plates, sheets, or films in the garment 105 and in the receptacle 1145 may be utilized to provide communication via capacitive coupling between one or more components of the receptacle 1145 and one or more components of the garment 105.

In some embodiments, in addition to or as an alternative to receptacles 1145, external medical device 100 may include one or more receptacles 145 as disclosed in commonly owned U.S. Pat. No. 9,008,801 disposed proximate respective therapy electrodes.

Arrangement and Interconnection of Conductive Gel Receptacles

In some embodiments, multiple receptacles 1145 in embodiments of the disclosed external medical device 100 are coupled to one another and/or to a common distribution node by one or more signal lines and/or fluid pressure conduits and/or gel conduits. The common distribution node may be included in various portions of the garment 105, for example, the monitor 125 or gel deployment control unit 130 or on one of the receptacles 1145, or may be a dedicated unit disposed, for example, on the belt 110 or other part of the garment 105. The common distribution node may provide communication between the receptacles 1145, for example, one or more electrical or electronic components of the receptacles, and one or more components of the garment 105, for example, alarm module 120 and/or monitor 125. The signal lines can include electrical conductors electrically connected to any of the embodiments of the connection port 1210 described above. The signal lines may be utilized to transfer communication signals between components of the external medical device and/or may be utilized to conduct current to receptacles 1145 that are included in therapy electrodes 135, 140 of the external medical device, for example, to deliver a defibrillation shock or pacing pulses to a subject. In embodiments where a receptacle 1145 does not contain any electrical components and is not part of a therapy electrode, the receptacle 1145 may not have any signal line connected to it. Features, for example, fluid pressure source(s) and/or electrical or electronic components (e.g., gel deployment control unit 1130, sensing circuit 1225, activator circuit 1230 pressure sensor 1220, and/or battery 1215) may be shared among the multiple receptacles 1145.

Figure 6:
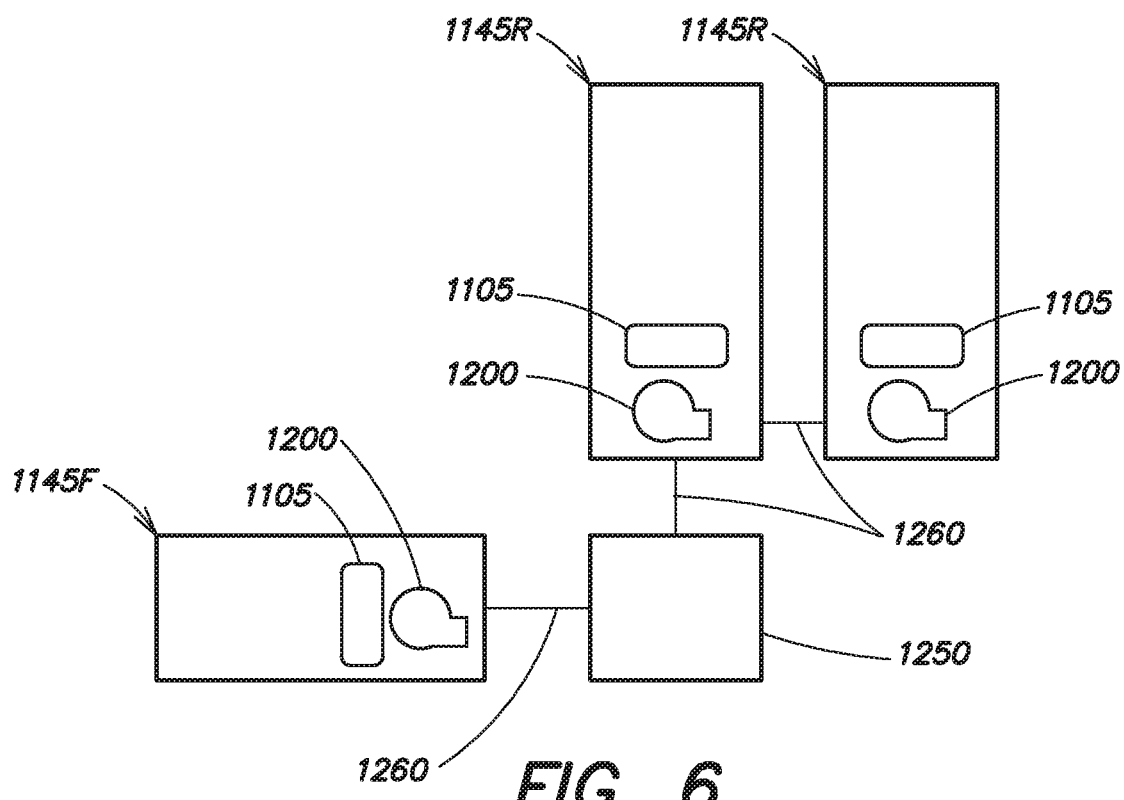
FIG. 6 is a schematic illustration of a plurality of receptacles for use in embodiments of an external medical device and interconnections between the plurality of receptacles.
Figure 7:
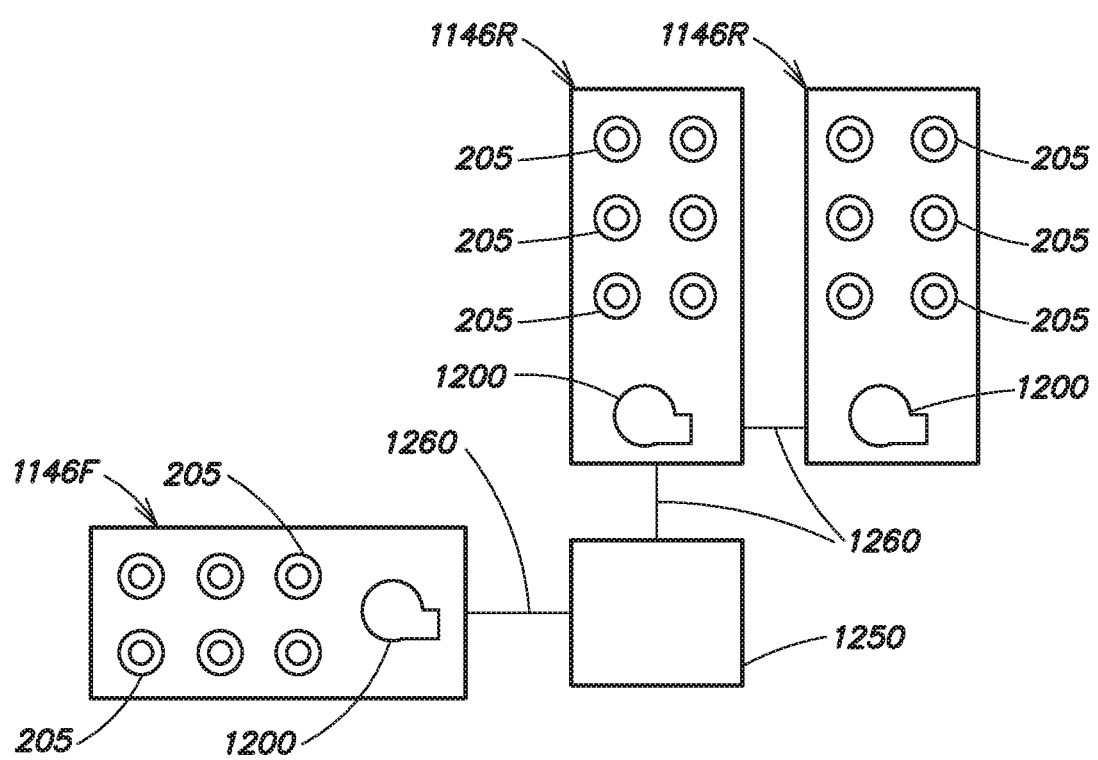
FIG. 7 is a schematic illustration of a plurality of receptacles for use in embodiments of an external medical device and interconnections between the plurality of receptacles.

For example, as illustrated in FIG. 6 a system includes two rear receptacles 1145R and one front receptacle 1145F coupled to a common distribution node 1250 by signal lines 1260. Each receptacle 1145R, 1145F includes its own gel chamber 1105 and pressure source, for example, fluid pumps 1200. It should be understood that in the example illustrated in FIG. 6 and those examples that follow the pressure source is not limited to a fluid pump 1200, but may be any fluid pressure source known in the art. Although illustrated as including embodiments of receptacle 1145, it should be appreciated that the embodiment illustrated in FIG. 6 as well as those illustrated in FIGS. 8-15 may be implemented with one or more of receptacles 1145 replaced with embodiments of receptacles 145 as disclosed in commonly owned U.S. Pat. No. 9,008,801, including multiple doses of conductive gel. For example, as illustrated in FIG. 7, the receptacles 1145R, 1145F of FIG. 6 may be substituted with receptacles 1146R, 1146F, respectively, which include multiple doses or reservoirs 205 of conductive gel. Receptacles 1146R, 1146F may be similar to embodiments of receptacles 145 as disclosed in commonly owned U.S. Pat. No. 9,008,801 and/or may include embodiments of gel capsules as disclosed in commonly owned U.S. patent application Ser. No. 13/314,799, titled "THERAPEUTIC DEVICE INCLUDING ACOUSTIC SENSOR," filed Jun. 25, 2014, the disclosure of which is incorporated herein by reference in its entirety.

Figure 8:
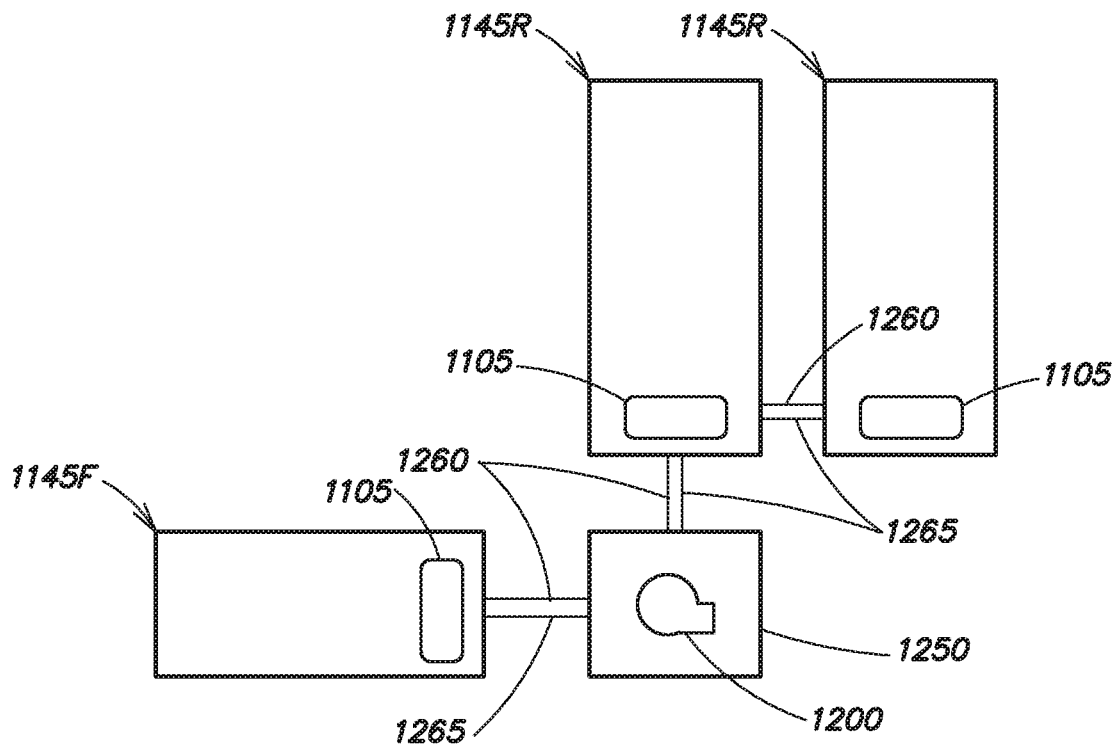
FIG. 8 is a schematic illustration of a plurality of receptacles for use in embodiments of an external medical device and interconnections between the plurality of receptacles.

FIG. 8 illustrates a system in which each receptacle 1145R, 1145F includes its own gel chamber 1105, but share a common fluid pump 1200. The fluid pump is disposed on the common distribution node 1250 and is in fluid communication with the gel chambers 1105 on each receptacle 1145R, 1145F through fluid pressure conduits 1265. Signal lines 1260 may also be provided, for communicating defibrillation and/or pacing pulses, as well as other electrical signals between components of the garment 105 and the receptacles 1145F, 1145R and/or between receptacles 1145F, 1145R and/or common distribution node 1250.

Figure 9:
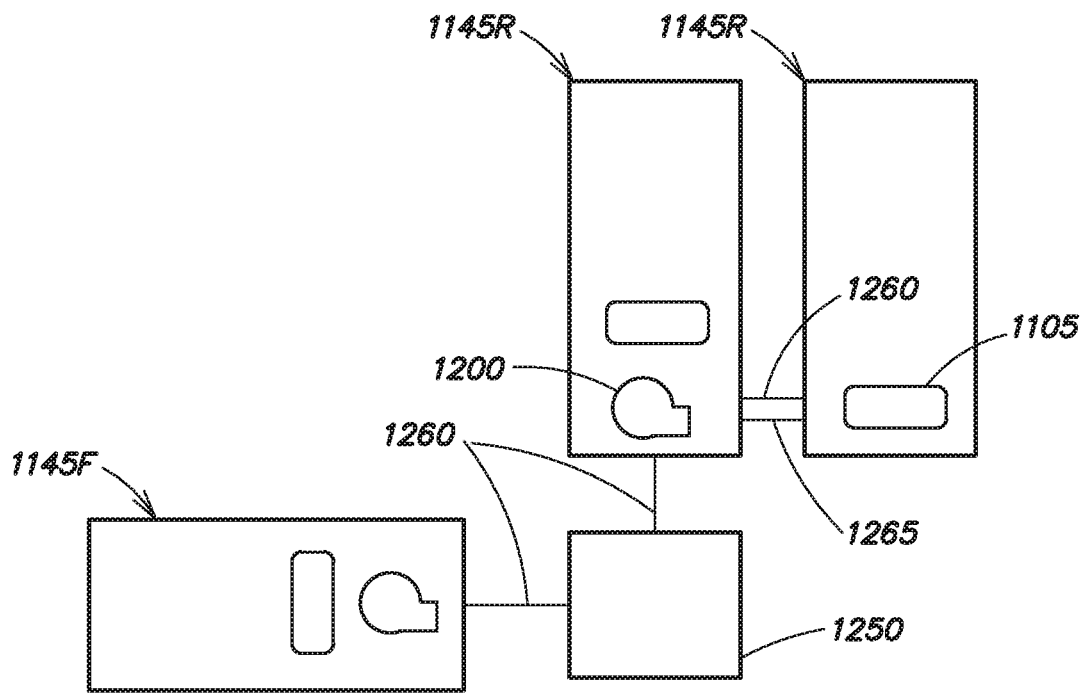
FIG. 9 is a schematic illustration of a plurality of receptacles for use in embodiments of an external medical device and interconnections between the plurality of receptacles.

In the example shown in FIG. 9, each receptacle 1145R, 1145F includes its own gel chamber 1105. The front receptacle 1145F includes its own fluid pump 1200. The rear receptacles 1145R share a common fluid pump 1200 mounted on one of the rear receptacles 1145R. A fluid pressure conduit 1265 allows for the fluid pump 1200 to deliver pressurized air to the gel chamber 1105 of the rear receptacle 1145R that it is not mounted on. Signal lines 1260 provide communication between the common distribution node 1250, the front receptacle 1145F, and the rear receptacles 1145R.

Figure 10:
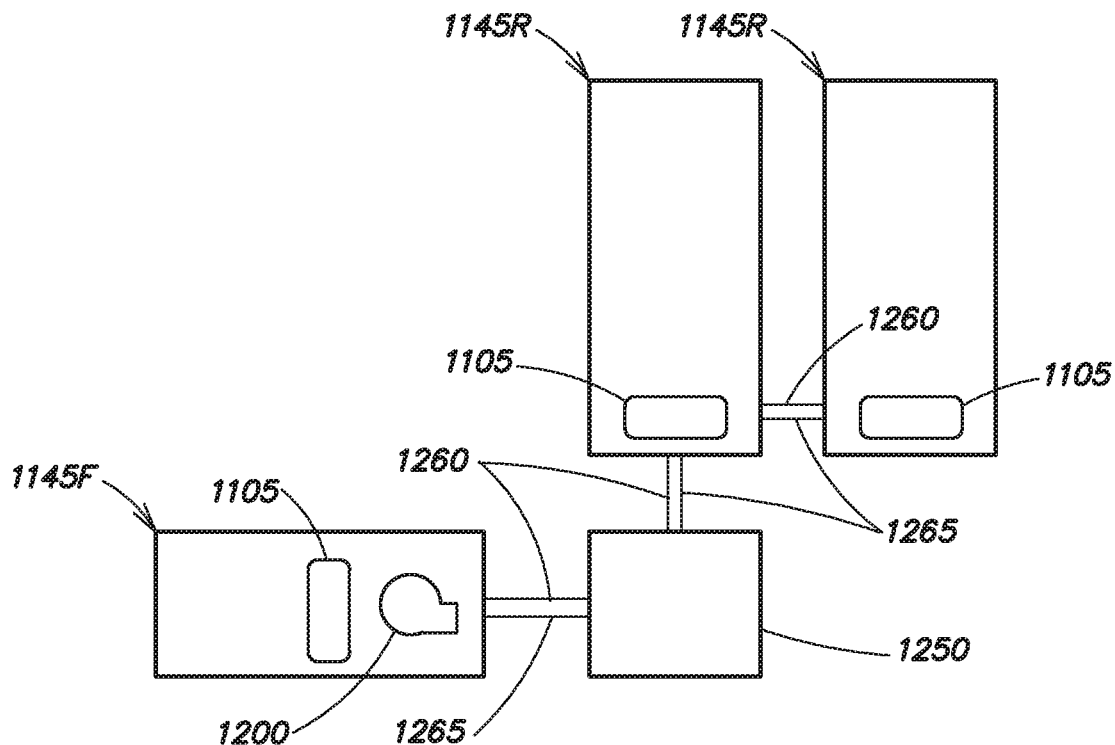
FIG. 10 is a schematic illustration of a plurality of receptacles for use in embodiments of an external medical device and interconnections between the plurality of receptacles.

FIG. 10 illustrates a system similar to FIG. 9, but wherein there is no fluid pump 1200 located on either of the rear receptacles 1145R. Rather, a single fluid pump 1200 is provided on the front receptacle 1145F. The fluid pump 1200 provided on the front receptacle 1145F controls release of conductive gel from each of the receptacles 1145F, 1145R. The rear receptacles 1145R may be considered "slave" receptacles controlled by front receptacle 1145F, which may be considered a "master" receptacle in the example of FIG. 10. Signal lines 1260 and fluid pressure conduits 1265 provide electrical and fluid communication, respectfully, between the front receptacle 1145F and the rear receptacles 1145R by way of the common distribution node 1250.

It should be appreciated that instead of the fluid pressure conduits 1265 and/or signal lines 1260 being routed through the common distribution node 1250, the fluid pressure conduit(s) 1265 and/or signal line(s) 1260 from the front receptacle 1145F may be directly coupled to the fluid inlet or a signal input, respectively, of one or both of the rear receptacles 1145R.

In other embodiments, any one of the receptacles may be a "master" receptacle and the other receptacles may be "slave" receptacles. The front receptacle 1145F and two rear receptacles 1145R can be connected as a group, with one of the three of receptacles containing the fluid pump 1200. Two of the receptacles can be in a "slave" relationship to the receptacle containing the fluid pump 1200 (the "master" receptacle). In some embodiments, each of the three receptacles can contain their own gel chambers 1105. As such, the fluid pump 1200 can cause force fluid (e.g., air) through conduits that are in fluid connection with the gel chambers 1105.

In some examples, the "master" receptacle can include a gel chamber 1105 in communication with apertures on all three receptacles. In this configuration, the gel deployment electronics as described herein can cause the fluid pump 1200 to deploy the gel through the apertures on all three receptacles. For example, the gel chamber on the "master" receptacle can be fluidly connected through a gel conduit to the apertures of the "slave" receptacles. In this scenario, the gel can be directed from the gel chamber 1105 on the "master" receptacle through the gel conduit and released from the apertures in each of the receptacles. In some implementations, after treatment, each of the "slave" receptacles can be user-replaceable (or replaceable during servicing), while the "master" receptacle may be retained.

Figure 11:
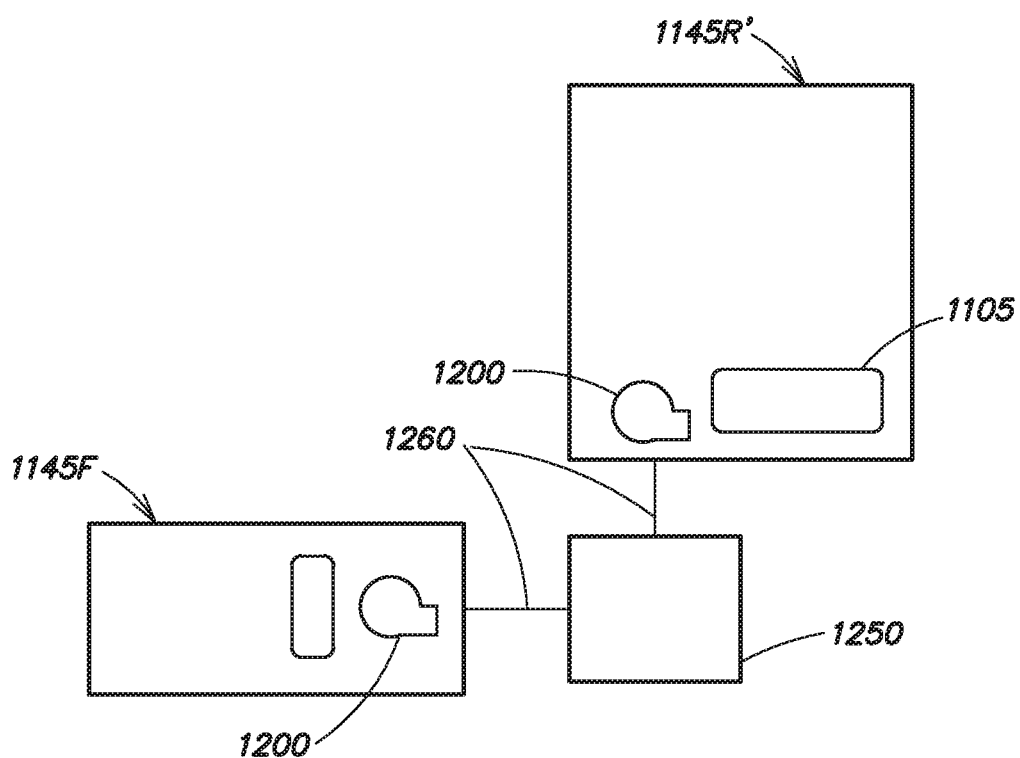
FIG. 11 is a schematic illustration of a plurality of receptacles for use in embodiments of an external medical device and interconnections between the plurality of receptacles.

In the example shown in FIG. 11, the two rear receptacles 1145R shown in FIG. 9 have been combined into a single larger rear receptacle 1145R' with a single larger gel chamber 1105 and the fluid pressure conduit 1265 has been eliminated. The front receptacle 1145F includes its own gel chamber 1105 and fluid pump 1200. Signal lines 1260 provide communication between the common distribution node 1250, the front receptacle 1145F, and the rear receptacle 1145R'.

Figure 12:
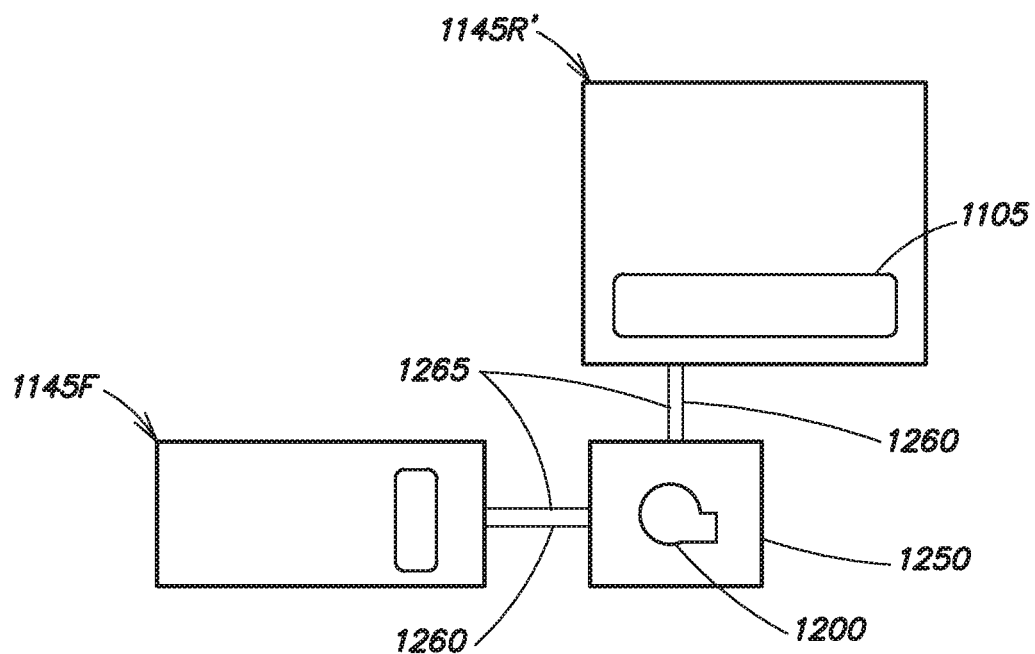
FIG. 12 is a schematic illustration of a plurality of receptacles for use in embodiments of an external medical device and interconnections between the plurality of receptacles.

The example illustrated in FIG. 12 includes a single larger rear receptacle 1145R' and a front receptacle 1145F, each with its own gel chamber 1105. The receptacles 1145R' and 1145F share a common fluid pump 1200 mounted on the common distribution node 1250 and fluidly connected to the gel chambers 1105 of the receptacles 1145R' and 1145F through fluid pressure conduits 1265. Signal lines 1260 may also be provided for communicating defibrillation and/or pacing pulses, as well as other electrical signals, between components of the garment 105 and the receptacles 1145F, 1145R' and/or between receptacles 1145F, 1145R' and/or common distribution node 1250.

Figure 13:
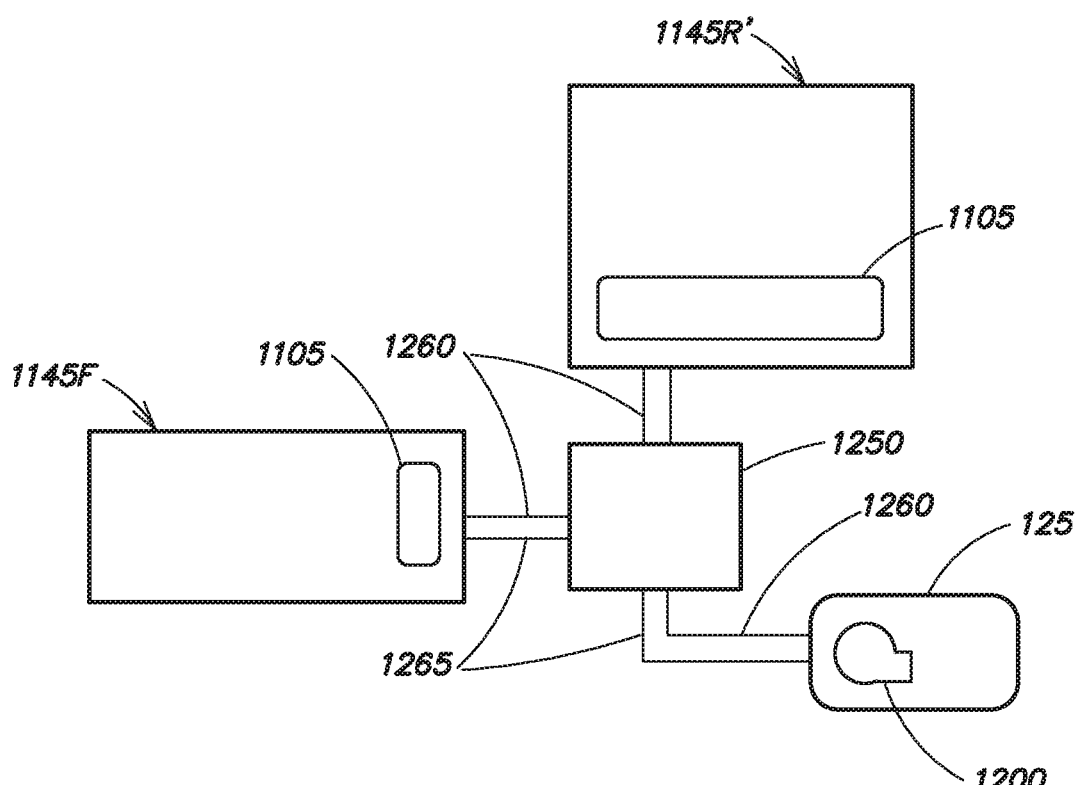
FIG. 13 is a schematic illustration of a plurality of receptacles for use in embodiments of an external medical device and interconnections between the plurality of receptacles and another component of the external medical device.

The example illustrated in FIG. 13 includes a single larger rear receptacle 1145R' and a front receptacle 1145F, each with its own gel chamber 1105. The receptacles 1145R' and 1145F share a common fluid pump 1200 mounted on a separate component of the garment 105, for example, the monitor 125. The fluid pump 1200 is fluidly connected to the gel chambers 1105 of the receptacles 1145R' and 1145F through fluid pressure conduits 1265 and through the common distribution node 1250. Signal lines 1260 may also be provided, for communicating defibrillation and/or pacing pulses, as well as other electrical signals between components of the garment 105, for example, monitor 125 and the receptacles 1145F, 1145R' and/or between receptacles 1145F, 1145R' and/or common distribution node 1250.

Figure 14:
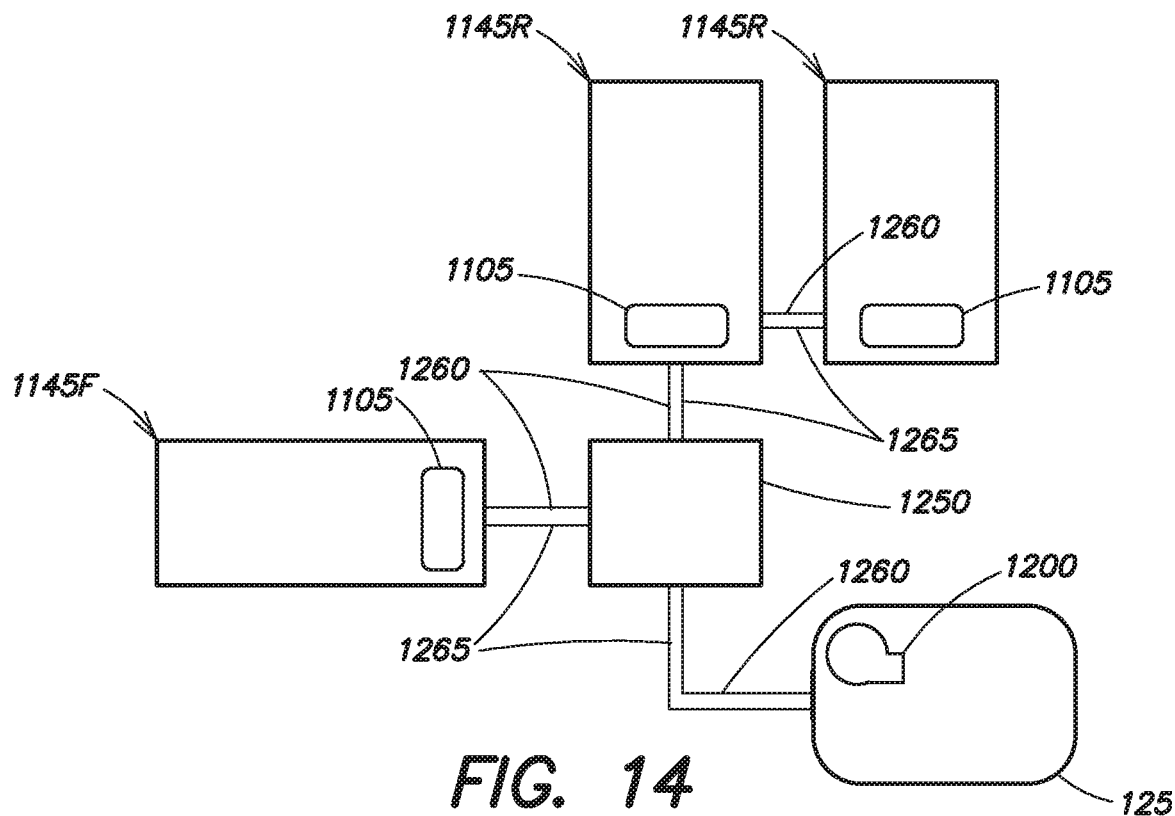
FIG. 14 is a schematic illustration of a plurality of receptacles for use in embodiments of an external medical device and interconnections between the plurality of receptacles and another component of the external medical device.

The example illustrated in FIG. 14 is similar to that illustrated in FIG. 13, with the single larger rear receptacle 1145R' split into two smaller sized receptacles 1145R. A fluid pressure conduit 1265 fluidly couples the receptacles 1145R so that pressurized air from the fluid pump 1200 can reach the gel chambers 1105 of both of the receptacles 1145R. Signal lines 1260 may also be provided, for communicating defibrillation and/or pacing pulses, as well as other electrical signals between components of the garment 105, for example, monitor 125 and the receptacles 1145F, 1145R and/or between receptacles 1145F, 1145R and/or common distribution node 1250.

Figure 15:
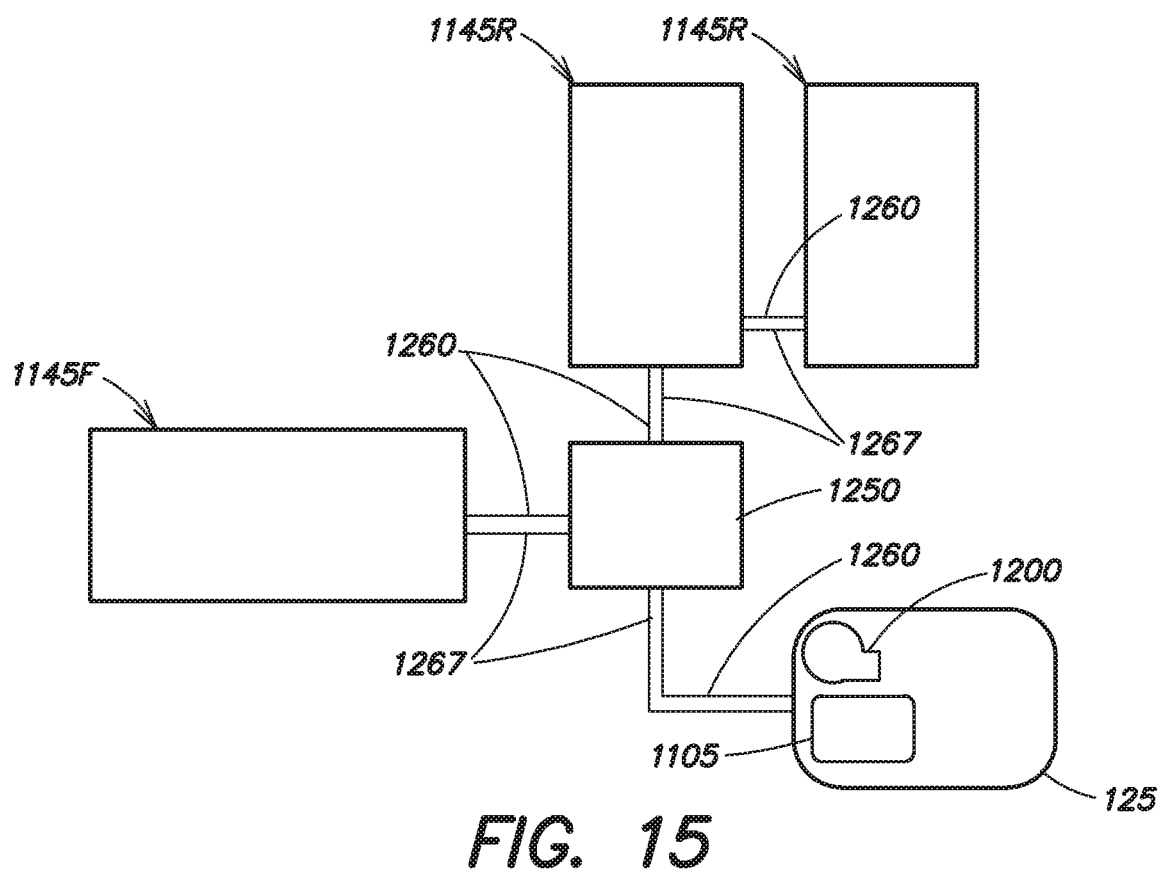
FIG. 15 is a schematic illustration of a plurality of receptacles for use in embodiments of an external medical device and interconnections between the plurality of receptacles and another component of the external medical device.

In the example shown in FIG. 15, none of the receptacles 1145F, 1145R includes its own fluid pump 1200 or gel reservoir 1105. Rather, a common fluid pump 1200 and large gel reservoir 1105 are disposed on a separate component of the garment 105, for example, the monitor 125. Conductive gel is directed into each of the receptacles 1145F, 1145R from the common large gel reservoir 1105 through gel conduits 1267 and through the common distribution node 1250. Signal lines 1260 may also be provided for communicating defibrillation and/or pacing pulses, as well as other electrical signals, between components of the garment 105, for example, monitor 125 and the receptacles 1145F, 1145R and/or between receptacles 1145F, 1145R and/or common distribution node 1250.

Figure 16:
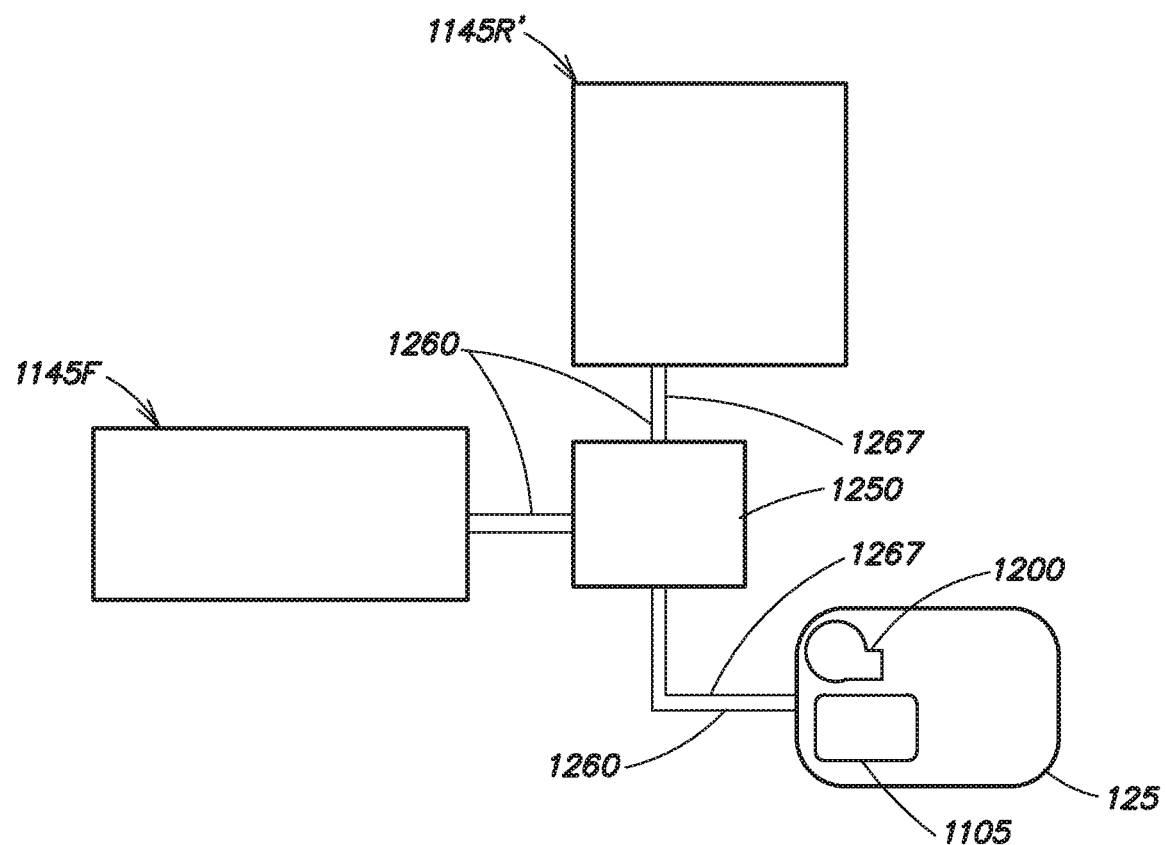
FIG. 16 is a schematic illustration of a plurality of receptacles for use in embodiments of an external medical device and interconnections between the plurality of receptacles and another component of the external medical device.

The example shown in FIG. 16 is similar to that shown in FIG. 15, with the two separate rear receptacles 1145R combined into a single large rear receptacle 1145R'. The fluid pressure conduit 1165 between the two rear receptacles 1145R of FIG. 15 is eliminated. Signal lines 1260 may be provided for communicating defibrillation and/or pacing pulses, as well as other electrical signals between components of the garment 105, for example, monitor 125 and the receptacles 1145F, 1145R and/or between receptacles 1145F, 1145R and/or common distribution node 1250.

Device Features

In one embodiment, at least one of first therapy electrode 135 and second therapy electrode 140 includes conductive thread. In one embodiment, at least one of first therapy electrode 135 and second therapy electrode 140 consists only of conductive thread. In one embodiment, at least one of first therapy electrode 135 and second therapy electrode 140 includes conductive thread as well as additional electrode components, such as a conductive element that may be stitched into garment 105 with the conductive thread. In such embodiments, a receptacle 1145 that does not include a conductive layer may be associated with each therapy electrode 135, 140 to dispense conductive gel between the electrodes 135, 140 and the body of a subject prior to the delivery of electrical energy, for example, a defibrillation shock or pacing pulses, to the subject through the therapy electrodes.

In one embodiment, when the subject is defibrillated or paced, conductive gel released from receptacles 1145 reduces impedance between first therapy electrode 135 and second therapy electrode 140 (or conductive thread, metallic surfaces, or combinations thereof that form a surface of electrodes 135, 140) and the subject's skin. The impedance reduction when conductive gel is released from receptacles 1145 improves the efficiency of energy delivery from therapy controller 115 to the subject and reduces the chance of skin damage in the form of, for example, burning, reddening, or other types of irritation to the skin.

Figure 17:
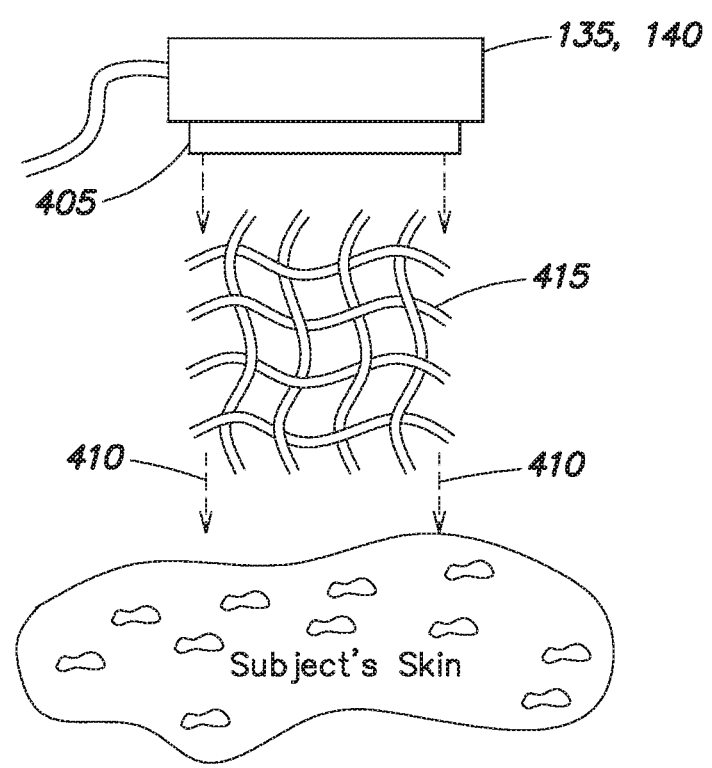
FIG. 17 is a schematic diagram depicting the interface between a therapy electrode and a subject's skin in accordance with an embodiment.

FIG. 17 depicts an example of conductive gel entering the area between a therapy electrode and the subject's skin. Conductive gel may also be similarly disposed between sensing electrode 150 and the subject's skin. In one embodiment, conductive gel enters the area between conductive surface 405 of electrode 135 or 140 and the subject's skin and forms a conduction path 410 from electrode 135 or 140 to the subject's skin. The conductive gel can cover conductive thread or mesh fabric 415 that is part of garment 105 and portions of which can be disposed between subject's skin and electrode 135 or 140. In the embodiment shown in FIG. 17, the therapy electrode 135, 140 may be formed from a receptacle 1145 and the conductive surface 405 may correspond to a conductive surface, for example, conductive surface 1160 disposed on the receptacle 1145.

In one embodiment, after the conductive gel has been deployed to facilitate treatment, receptacles 1145 can be replaced without replacing additional garment 105 components, for example, belt 110. For example, belt 110 need not be replaced, and soiled areas of belt 110 can be cleaned. As a result the subject need not wait for a replacement belt 110, and need not manually add conductive gel to electrodes 135, 140 to maintain an appropriate electrical connection as a precaution in case additional treatment (e.g., shocks) become necessary while waiting for a replacement belt.

In one embodiment, permanently housing or integrating at least one of first therapy electrode 135 and second therapy electrode 140 in belt 110 (or elsewhere in external medical device 100) ensures that they are properly inserted and configured to deliver a shock to the subject because the subject cannot, in this example, tamper with their location or configuration, or accidentally improperly insert them into belt 110 (e.g., backwards, not properly electrically coupled, or facing the wrong way). In one embodiment, at least one surface or a pad associated with at least one of first therapy electrode 135 and second therapy electrode 140 faces the subject's skin to make a sufficient low impedance current path between at least one of first therapy electrode 135 and second therapy electrode 140 and the subject's skin when the conductive gel is deployed. For example, first therapy electrode 135 or second therapy electrode 140 can be housed in a pocket of garment 105, with a surface or side wall of garment 105 between the subject's skin and electrode 135 or electrode 140 having a metallic mesh pattern. The metallic mesh can include silver or other conductive metals to lower impedance between the subject's skin and the conductive surface of electrode 135 or electrode 140.

In one embodiment, at least one of first therapy electrode 135 and second therapy electrode 140 are part of or integral to at least one of external medical device 100, garment 105, or belt 110, with conductive gel reservoir 1105 and a deployment mechanism configured in replaceable receptacle 1145.

Figure 18:
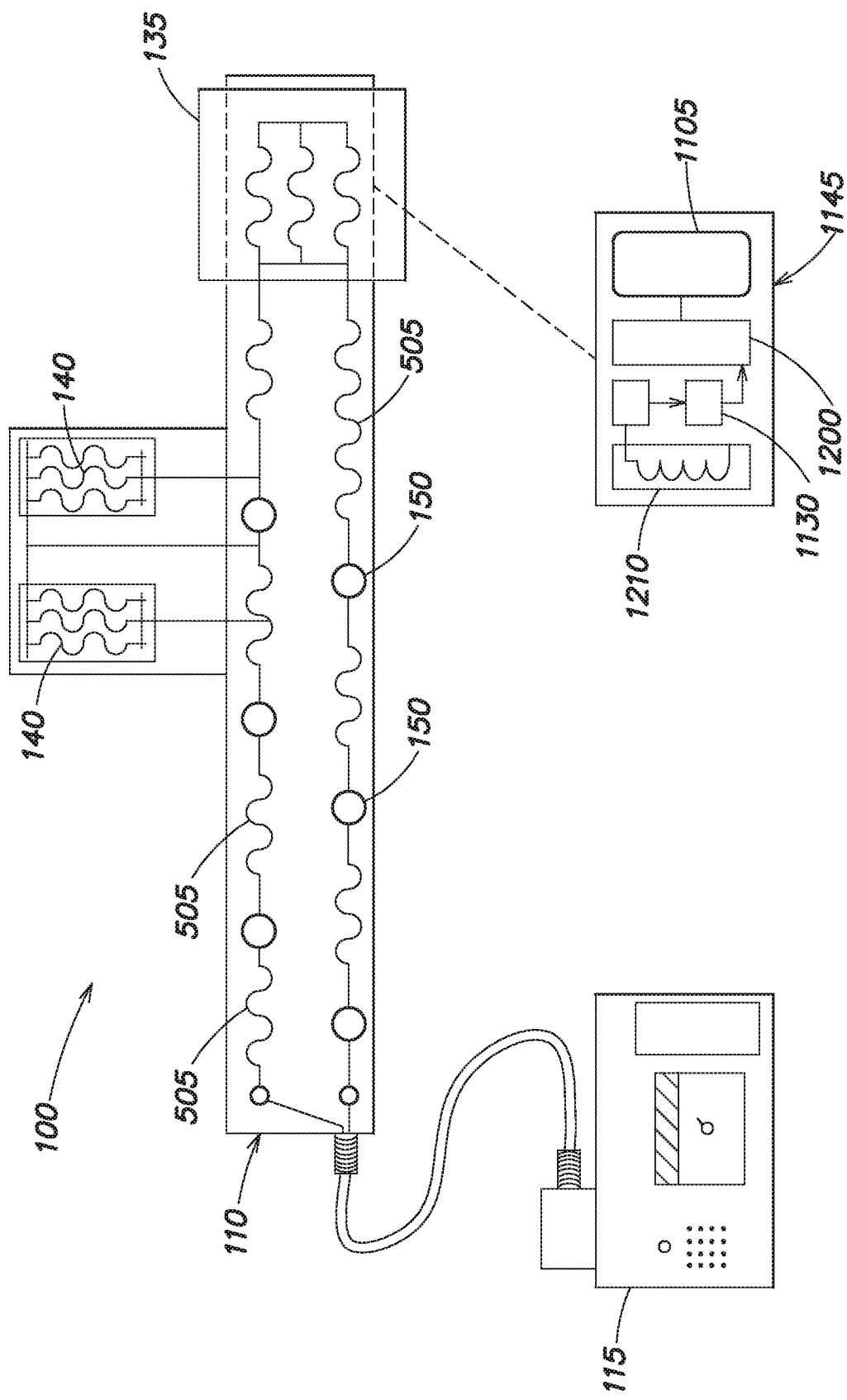
FIG. 18 is a schematic diagram depicting components of an external medical device in accordance with an embodiment.

FIG. 18 illustrates components of external medical device 100 according to one embodiment, with sensing electrodes 150 including at least one EKG (or ECG) electrocardiogram sensor, conductive thread 505 woven into belt 110 of garment 105, and receptacle 1145 disposed proximate to first therapy electrode 135 in belt 110.

In one embodiment, control unit 1130 instructs receptacle 1145 to release the conductive gel included in conductive gel reservoir 1105. The released conductive gel reduces impedance between the subject's skin and first therapy electrode 135 and second therapy electrode 140. Therapy controller 115 applies treatment (e.g., a shock) to the subject via first therapy electrode 135 and second therapy electrode 140. During treatment, current follows a path between the subject's skin and first therapy electrode 135 and second therapy electrode 140 via the conductive gel. In one embodiment, after treatment, the subject removes and discards or recycles the spent receptacles 1145, washes any soiled areas of garment 105, for example, portions of belt 110, and installs replacement receptacles 1145. The subject or external medical device 100 may carry spare receptacles 1145. In one embodiment, the subject may wear a backup external medical device 100 during this changeover period.

In one embodiment external medical device 100 indicates to the subject whether or not receptacles 1145 have been properly inserted. For example, audio, visual, or haptic signals, or combinations thereof, can be provided by alarm module 120 or monitor 125. By incorporating at least one of first therapy electrode 135 and second therapy electrode 140 and associated wiring into external medical device 100, garment 105 is more comfortable for the subject wearing it. There are fewer components to assemble and maintain, and to cause subject discomfort during use.

Receptacle 1145 may also include a control unit 1130 to control conductive fluid delivery and to communicate with therapy controller 115, and a connection port 1210, for example, a winding of an induction coil (or other interface such as a connector) to interface with one or more components of the garment 105, for example, alarm module 120 and/or monitor 125.

In one embodiment, the conductive gel includes a gel, liquid, or other material that lowers impedance for energy transfer between electrodes 135, 140, and the subject. The conductive gel can remain on the subject's skin for a period of time, for example, several hours before it is removed, and the conductive gel remains functional as an impedance reducing material during this time period. The conductive gel in one embodiment also has sufficient shelf life to remain dormant for a period of time prior to use. In one embodiment, receptacle 1145 indicates an expiration date of the conductive gel. Control unit 1130 can determine the expiration date and, upon or prior to expiration, indicate via alarm module 120 or monitor 125 that receptacle 1145 should be replaced.

In one embodiment, receptacle 1145 can include control unit 1130 to communicate with therapy controller 115 to release the conductive gel at the appropriate time. Information communicated between the receptacle 1145 and therapy controller (via at least one control unit 1130 located on receptacle 1145, therapy controller 115, garment 105, or combinations thereof) includes: the presence or absence of receptacle 1145; whether or not the conductive gel has been released from receptacle 1145; a fault condition that can occur if receptacle 1145 has been commanded to release the conductive gel but the conductive gel has failed to release; the integrity of gas and/or fluid chambers associated with pressure sensor 1220 that are configured to deliver pressure to conductive gel reservoir 1105 to release the conductive gel; and the age of the conductive gel based, for example, on the date of manufacture of the conductive gel or of receptacle 1145.

In one embodiment, receptacles 1145 are replaceable subunits of garment 105. The subject can be supplied with spare receptacles 1145 so that spent or consumed receptacles 1145 can be quickly replaced in the event of their use during treatment, providing continuous or essentially continuous protection without having to replace belt 110, electrodes 135 or 140, or other wearable therapeutic device components. Receptacle 1145 may also include control unit 1130 to control conductive fluid delivery and to communicate with therapy controller 115, and connection port 1210 (for example, a winding of an induction coil or another form of connector as discussed above) to interface with garment 105.

Figure 19:
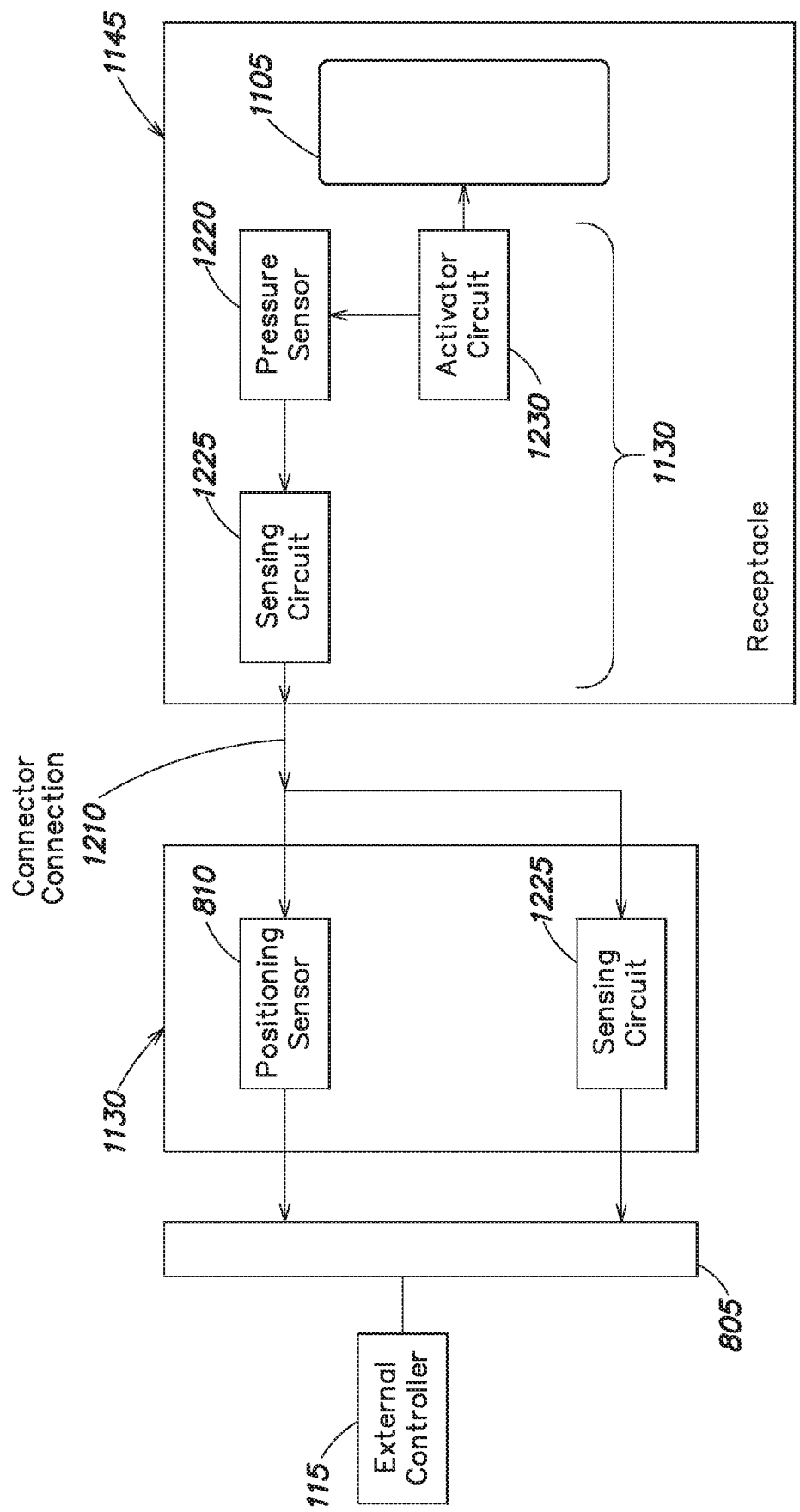
FIG. 19 is a schematic diagram depicting communication between a receptacle of a wearable therapeutic device and a therapy controller of the wearable therapeutic device in accordance with an embodiment.

FIG. 19 illustrates an example of the connection between receptacle 1145 and therapy controller 115 via interface 805. FIG. 19, as well as FIGS. 20 and 21 described below, illustrate positioning sensing circuits 1225 located external to receptacle 1145, for example, in a control unit 1130 separate from the receptacle 1145, and on receptacle 1145. Some embodiments may have redundant sensing circuits 1225 as illustrated or sensing circuits 1225 configured to sense different parameters, while in other embodiments, only a single sensing circuit 1225 is provided, for example, within the control unit 1130, if separate from the receptacle 1145, or in the receptacle 1145 itself.

In one embodiment, pressure sensor 1220 detects if gel conduit 1165 been compromised. The gel conduit 1165 may be purged such that its contents change color when exposed to air. In one embodiment, there can be a vacuum on the gel conduit 1165, and pressure sensor 1220 detects when the gel conduit 1165 has been compromised based on changes in its pressure. In one embodiment, therapy controller 115 detects when, or is informed by sensing circuit 1225 that the conductive fluid has been released, when receptacle 1145 has a fault condition, is missing, or improperly inserted, and when the conductive fluid is expired or approaching expiration. Therapy controller 115 may then indicate this status condition to the subject via its own monitor or interface, or via alarm module 120 or monitor 125, so that the subject can take the appropriate action.

Figure 20:
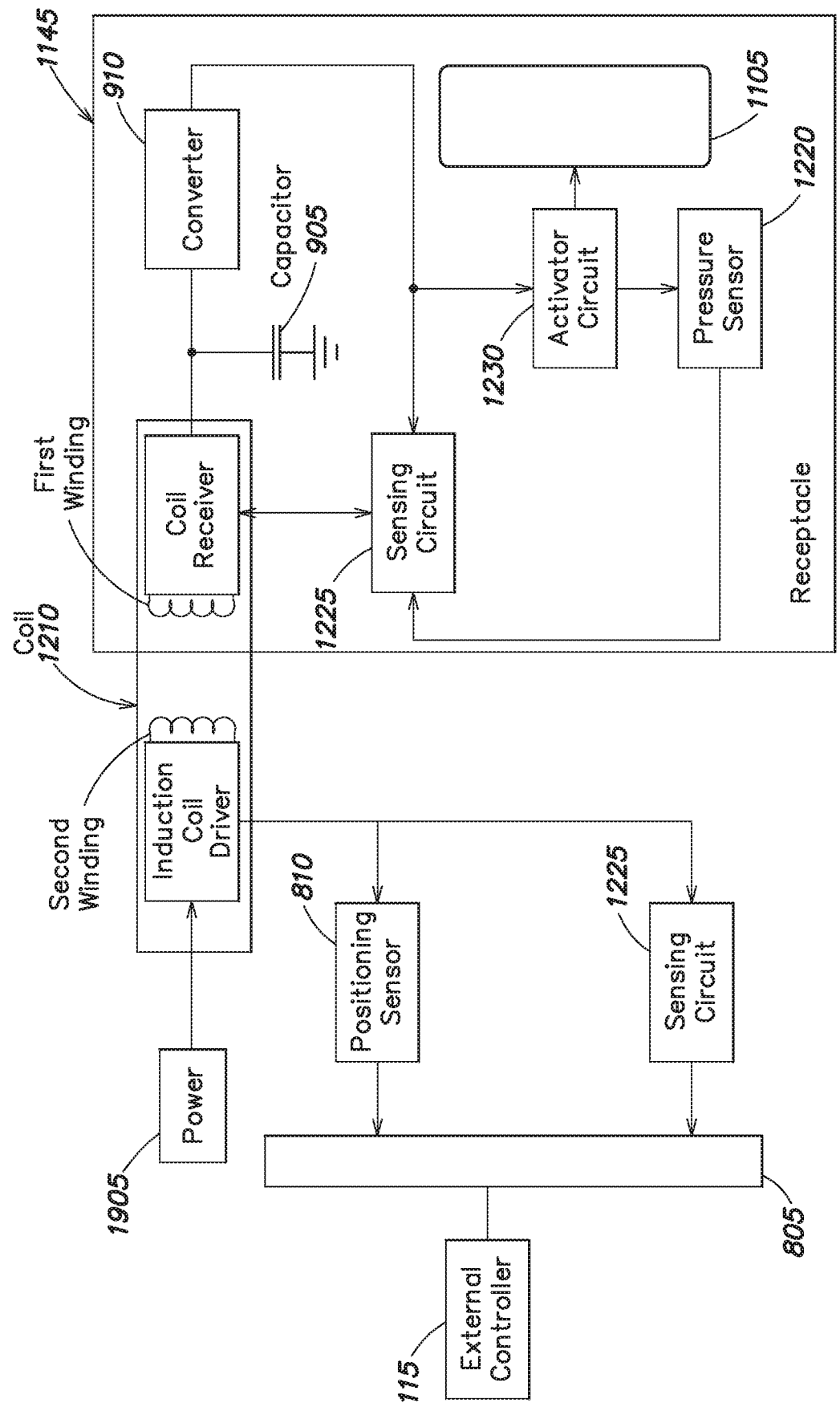
FIG. 20 is a schematic diagram depicting communication between a receptacle of an external medical device and a therapy controller of the external medical device in accordance with an embodiment.

With reference to FIGS. 4 and 20, among others, a connection port 1210 forming a connection between receptacle 1145 and therapy controller 115 via garment 105 can incorporate an induction coil, a capacitive coupling, RF and/or IR link, other wireless connections, magnets, or can be a hardwire connection using a connector. The connection allows receptacle 1145 to be removed and replaced, for example, after the conductive fluid has been released at the appropriate time during treatment.

Portions of gel deployment control unit 1130 can be located entirely on receptacle 1145, entirely external to receptacle 1145, or both on receptacle 1145 and external to receptacle 1145 at other locations of external medical device 100. For example, components of any of sensing circuit 1225, pressure sensor 1220, positioning sensor 810, and activator circuit 1230 can be part of receptacle 1145, external to receptacle 1145, or connected to receptacle 1145 via a connection port 120, for example, an induction coil.

Figure 21:
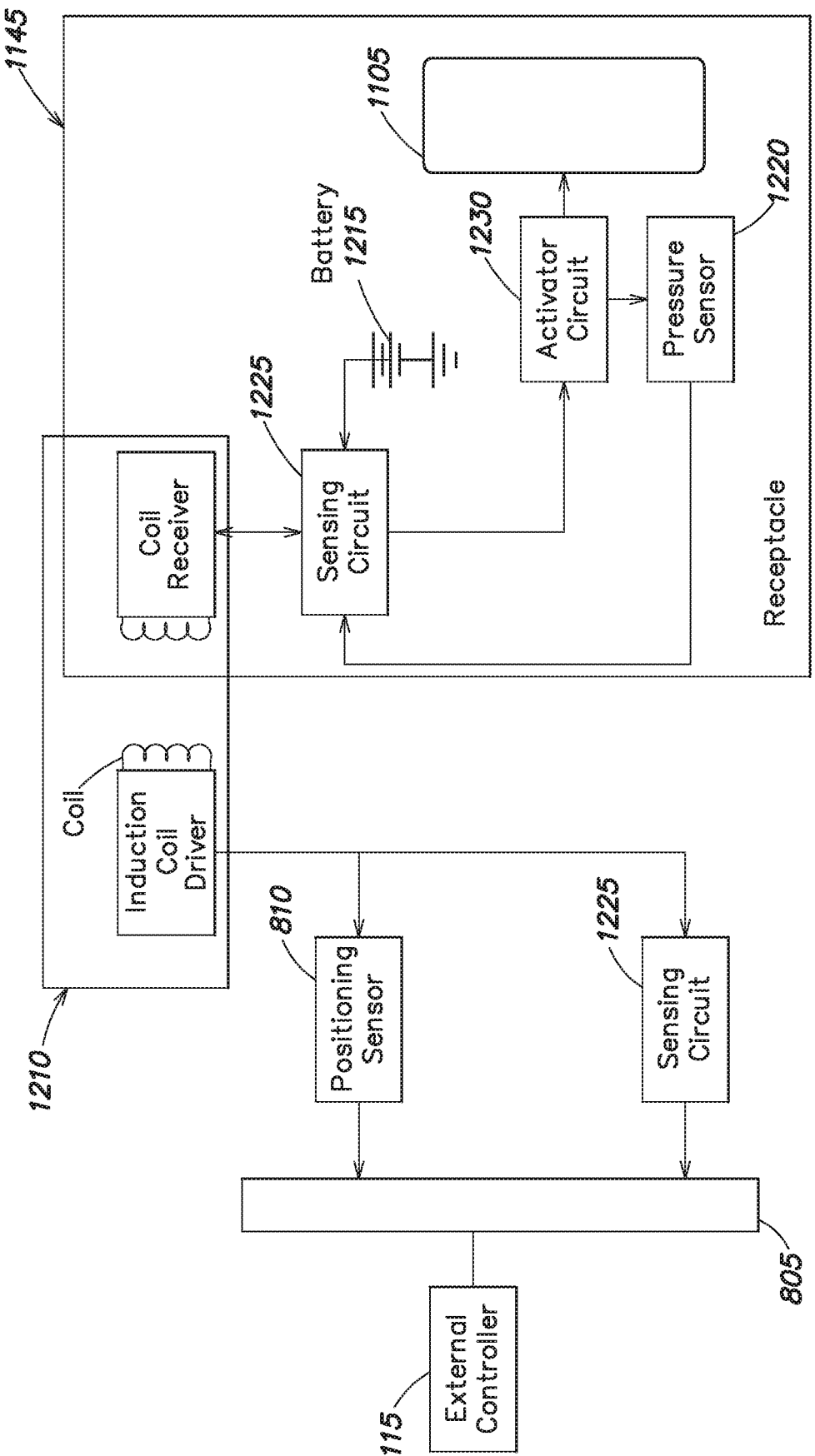
FIG. 21 is a schematic diagram depicting communication between a receptacle of an external medical device and a therapy controller of the external medical device in accordance with an embodiment.

FIG. 20 and FIG. 21 depict examples where a connection port 1210 including an induction coil connects receptacle 1145 with garment 105 and therapy controller 115. In one embodiment, receptacle 1145 electromagnetically couples with garment 105 via at least one induction coil. In one embodiment, a first winding of the induction coil is disposed on receptacle 1145 and a second winding is disposed in garment 105. When receptacle 1145 is inserted into place in garment 105, the first and second windings are brought into position to form an electromagnetic coupling between receptacle 1145 and therapy controller 115 via garment 105 and its wiring. In one embodiment, the induction coil permits close proximity communication and power transfer between receptacle 1145 and garment 105 (and garment 105's components) without a hardwired connection via a connector. The induction coil may be at least partially woven, sewn, or embroidered with conductive elements into garment 105 or components thereof such as therapy pads of electrodes 135, 140. In one embodiment, as illustrated in FIG. 20, power for receptacle 1145 is provided by capacitor 905, with the induction coil transferring power to receptacle 1145 from power supply 1905 to charge capacitor 905. In one embodiment, converter 910 converts AC power from power supply 1905 to DC power that can be provided to any of sensing circuit 1225, pressure sensor 1220, activator circuit 1230, or positioning sensor 810. Power for receptacle 1145 can also be provided by battery 1215 as illustrated in FIG. 21.

In one embodiment, receptacles 1145 are packaged as individual self contained units. For example, in a wearable therapeutic device including one first therapy electrode 135 and two second therapy electrodes 140, three receptacles 1145 (one for each of the three therapy electrodes) can be identical.

Figure 22:
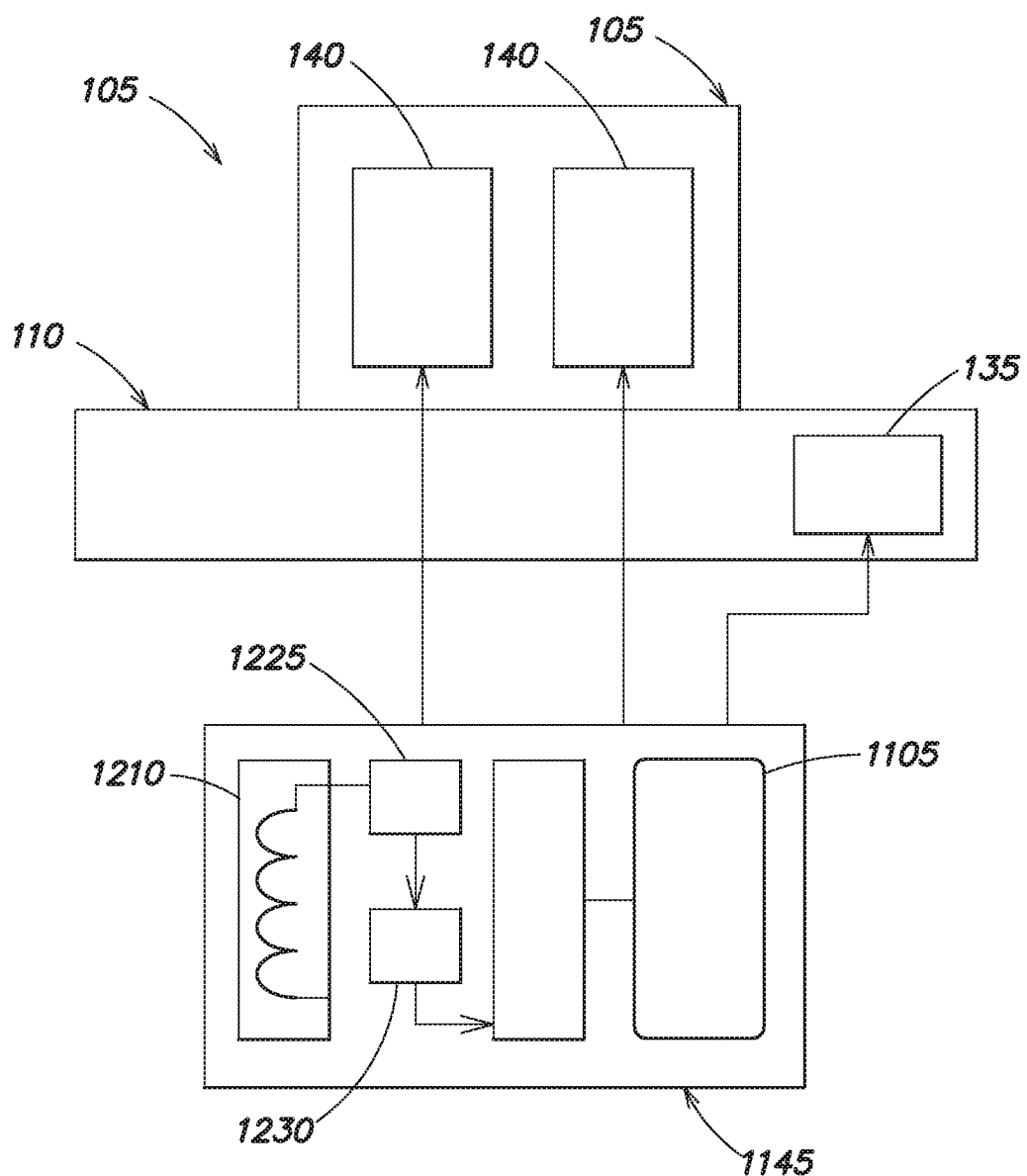
FIG. 22 is a schematic diagram depicting an external medical device in accordance with an embodiment.

In one embodiment, receptacles 1145 are packaged as individual self contained units. For example, with one first therapy electrode 135 and two second therapy electrodes 140, three receptacles 1145 (one for each of the three therapy electrodes) can be identical, as illustrated in FIG. 22.

In one embodiment, garment 105 includes conductive thread 505 to form electrical connections between areas of garment 105 and between external medical device 100 components. First therapy electrode 135, second therapy electrode 140, and sensing electrode 150 can include conductive thread 505 or metallic surfaces sewn into garment 105. Conductive thread 505 can also provide connections between any of electrodes 135, 140, and 150 and battery powered wearable therapy controller 115. In one embodiment, sensing electrodes 150 pick up the subject's ECG (EKG) signals and provide those signals to therapy controller 115 and/or monitor 125. Therapy electrodes 135, 140 and the conductive fluid form part of a current path to transfer energy from therapy controller 115 to the subject.

Figure 23:
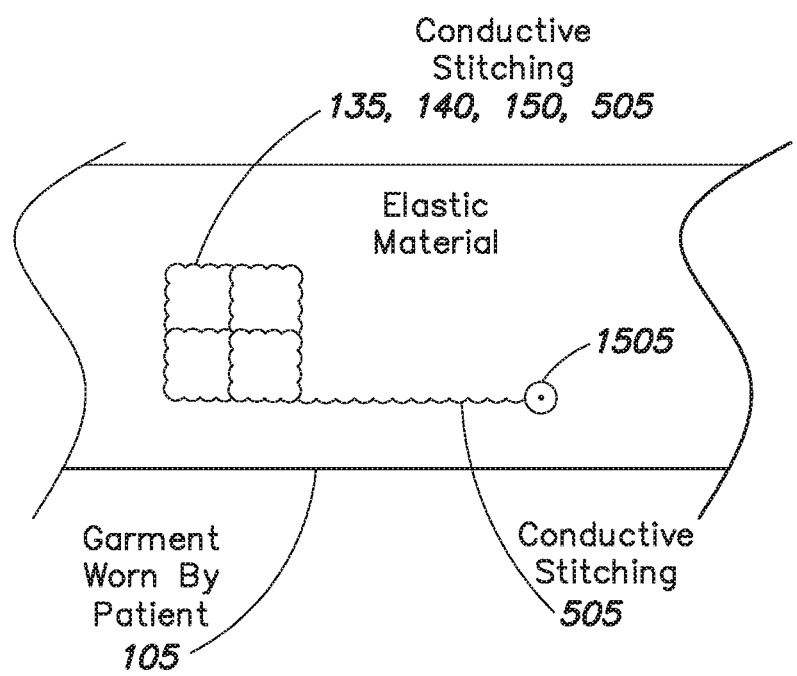
FIG. 23 is a schematic diagram depicting electrodes of an external medical device that include conductive stitching in accordance with an embodiment.
Figure 24:
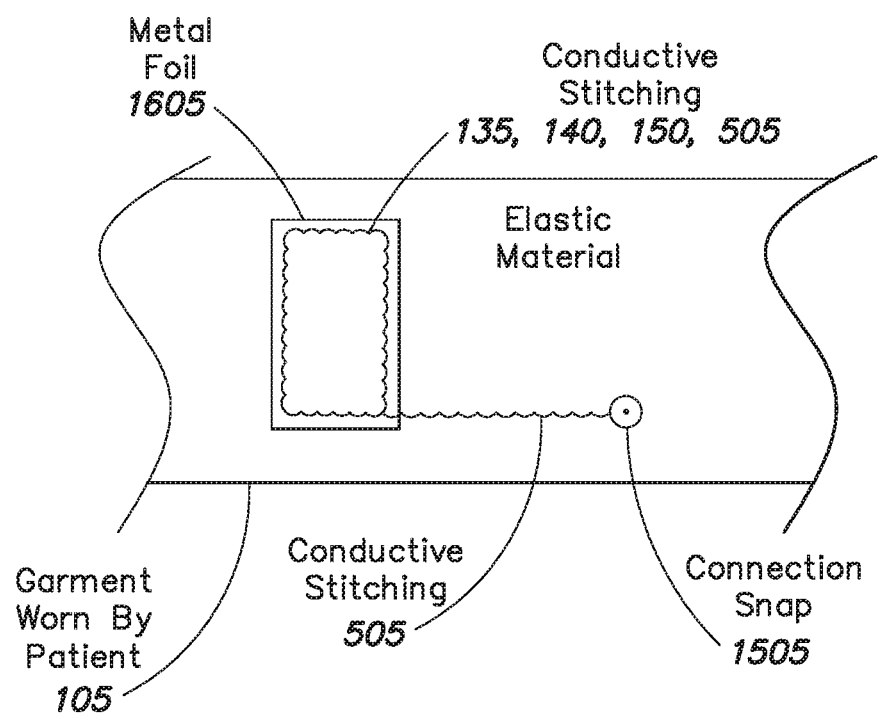
FIG. 24 is a schematic diagram depicting electrodes of an external medical device that include conductive stitching in accordance with an embodiment.

In one embodiment, electrodes 135, 140, and/or 150 include conductive stitching 505 in various patterns to achieve proper EKG sensing and to administer therapy. In one embodiment, at least one of electrodes 135, 140, and 150 include only conductive stitching 505. Garment 105 may include an elastic material. An example of this is illustrated in FIG. 23, where connection snap 1505 can electrically couple at least one of electrodes 135, 140, and 150 with other components of external medical device 100 such as garment 105, receptacles 1145 or therapy controller 115. In one embodiment, at least one of electrodes 135, 140, and 150 includes conductive stitching 505 that holds a metal foil 1605 or other conductive component in place in garment 105. In this example, at least a portion of at least one of electrodes 135, 140, and 150 includes conductive thread 505 and metal foil 1605. An example of this is illustrated in FIG. 24.

In one embodiment, conductive thread 505 is sewn into garment 105 (e.g., belt 110) in a zigzag pattern that can stretch as part of garment 105. This stretchable conductive thread stitching 505 connects therapy electrodes 135 and 140 with control unit 130 or other garment 105 components (e.g., therapy controller 115, receptacle 1145, and sensing electrode 150) in the absence of additional wires. Conductive thread (e.g., conductive wiring) 505 can face toward or away from the subject's skin. In one embodiment, conductive stitching 505 faces toward receptacle 1145 and away from the subject's skin so as to not irritate the subject. When the conductive fluid releases, it contacts the conductive thread 505 and spreads through at least a portion of garment 105 and contacts the subject's skin. In one embodiment, an elastic tension member of garment 105 is positioned proximate to receptacle 1145 to hold receptacle 1145 in position proximate to one of electrodes 135 and 140. When conductive stitching 505 faces toward the subject's skin, electrical contact between the electrodes 135 and/or 140 and the subject's skin can occur in the absence of conductive fluid.

Figure 25:
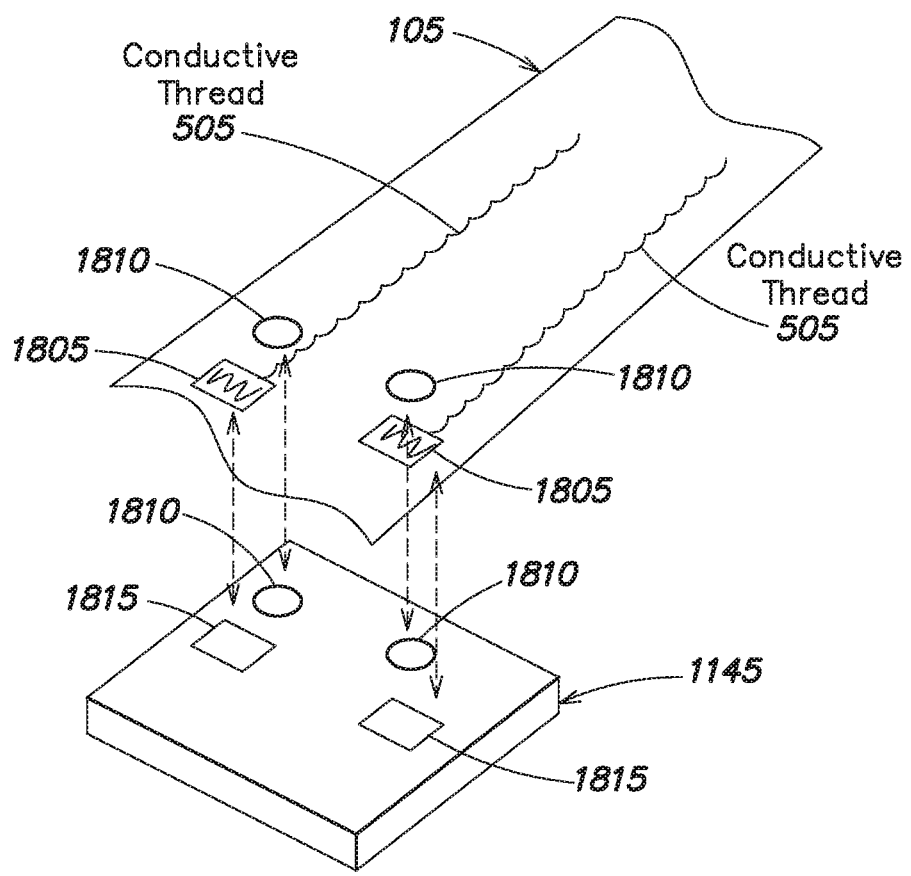
FIG. 25 is a schematic diagram depicting components of an external medical device in accordance with an embodiment.
Figure 26:
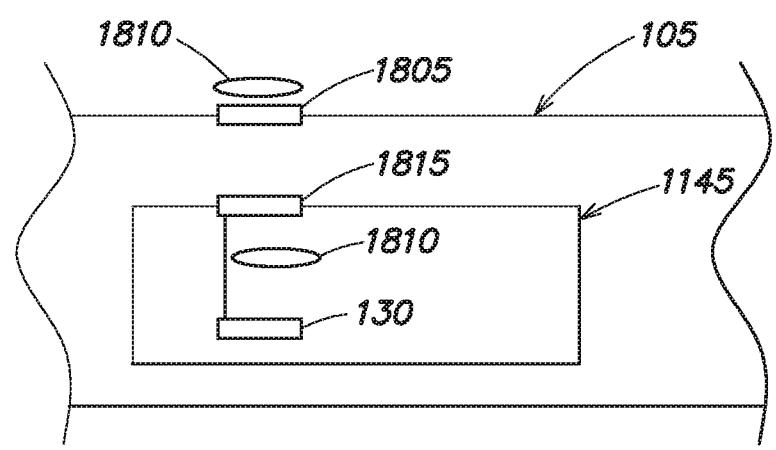
FIG. 26 is a schematic diagram depicting components of an external medical device in accordance with an embodiment.

FIG. 25 and FIG. 26 are schematic diagrams depicting an embodiment where garment 105 includes conductive pads 1805 and magnets 1810 to align garment 105 with receptacle 1145 to facilitate electrical coupling between garment 105 and receptacle 1145. Conductive pads 1805 may include conductive thread 505 or other textile materials woven into garment 105 to provide current from a current source to receptacles 1145. The current source can be housed within or remote from external medical device 100. In one example, magnets 1810 are disposed proximate to conductive pads 1805. Receptacle 1145 can also include magnets 1810. Magnets 1810 provide magnetic force (attractive or repulsive) between garment 105 and receptacle 1145 to align conductive pads 1805 with contact elements 1815 of receptacle 1145. For example, attractive magnetic forces between magnets 1810 on garment 105 and receptacle 1145 can indicate alignment between conductive pads 1805 and contact elements 1815 of receptacle 1145, or repulsive magnetic forces can indicate improper alignment, facilitating the insertion of receptacle 1145 into garment 105. Receptacle 1145 can include conductive contact elements 1815 that align with conductive pads 1805 when receptacle is properly positioned in garment 105. Forces from magnets 1810 align conductive contact elements 1815 with conductive pads 1805 to provide an electrical connection between components of garment 105 and receptacle 1145. Current may pass via this electrical connection, under control of control unit 130, to release conductive fluid from receptacles 1145. In one embodiment, receptacle 1145 is disposed in a pocket of garment 105, and magnets 1810 are disposed in garment 105 on opposite sides of receptacle 1145 when disposed in the pocket. In one embodiment, magnets 1810 are coated, for example in plastic, to protect from wear, damage (e.g., during washing), or high moisture conditions. In one embodiment, conductive pad 1805 is at least part of electrode 135, 140, or 150. In some embodiments, the magnets 1810 and the conductive pads 1805 on the garment may be combined into conductive magnetic elements. In some embodiments, the magnets 1810 and conductive contact elements 1815 on the receptacle 1145 may be combined into conductive magnetic contact elements.

In one embodiment, garment 105 includes snaps to align garment 105 with receptacle 1145 to facilitate electrical coupling between garment 105 and receptacle 1145. For example, snaps can fix garment 105 in position with contact elements 1815 aligned with conductive pads 1805.

The foregoing is illustrative and not limiting, having been presented by way of example. In particular, although many of the examples presented herein involve specific combinations of or system elements, it is understood that those acts and those elements may be combined in other ways. Acts, elements and features discussed only in connection with one embodiment are not excluded from a similar role in other embodiments.

Note that in FIGS. 1 through 26, the enumerated items are shown as individual elements. In actual implementations of the systems and methods described herein, however, they may be inseparable components of other electronic devices such as a digital computer. Thus, actions described above may be implemented at least in part in software that may be embodied in an article of manufacture that includes a program storage medium. The program storage medium includes data signals embodied in one or more of a carrier wave, a computer disk (magnetic, or optical (e.g., CD or DVD, or both)), non-volatile memory, tape, a system memory, and a computer hard drive. The program storage medium can include at least non-transient mediums, and the signals can include at least non-transient signals.

From the foregoing, it is appreciated that the wearable therapeutic device provided herein affords a simple and effective way to automatically apply and immediately provide lifesaving care to a subject during a cardiac event without any human intervention.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment in any manner consistent with the aspects and embodiments disclosed herein.

References to "or" should be construed as inclusive so that any terms described using "or" may indicate any of a single, more than one, and all of the described terms. Intervening embodiments, acts, or elements are not essential unless recited as such.

Where technical features in the drawings, detailed description or any claim are followed by references signs, the reference signs have been included for the sole purpose of increasing the intelligibility of the drawings, detailed description, and claims. Accordingly, neither the reference signs nor their absence have any limiting effect on the scope of any claim elements.

One skilled in the art will realize the systems and methods described herein may be embodied in various forms. The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A therapy electrode system comprising:
a garment configured to be worn about a torso of a patient;
a therapy electrode disposed in the garment and configured to deliver one or more electrical shocks to a body of the patient;
a replaceable gel cartridge disposed on the therapy electrode and configured to release a conductive gel onto the patient's skin at an interface between the therapy electrode and the patient's skin prior to the delivery of the one or more electrical shocks to the body of the patient at the interface between the therapy electrode and the patient's skin;
a fluid pump in fluid communication with the replaceable gel cartridge; and
a shell including a plurality of shell apertures, the therapy electrode configured to deliver the conductive gel from the replaceable gel cartridge to the patient's skin through the plurality of shell apertures.

2. The therapy electrode system of claim 1, wherein the fluid pump is removably coupled to the replaceable gel cartridge.

3. The therapy electrode system of claim 1, wherein the fluid pump comprises an air pump.

4. The therapy electrode system of claim 1, wherein the conductive gel is housed within a bladder disposed within the replaceable gel cartridge.

5. The therapy electrode system of claim 1, wherein the replaceable gel cartridge is disposed on a first side of the shell and the therapy electrode further comprises a conductive layer disposed on a second side of the shell.

6. The therapy electrode system of claim 5, wherein the conductive layer includes a plurality of conductive layer apertures, each of the plurality of conductive layer apertures circumscribing a respective shell aperture.

7. The therapy electrode system of claim 6, wherein each of the plurality of conductive layer apertures has a cross-sectional area greater than a cross-sectional area of the shell aperture that it surrounds.

8. The therapy electrode system of claim 1, comprising:
a plurality of therapy electrodes disposed in the garment; and
a monitor configured to monitor a physiological parameter of the patient utilizing the therapy electrode system.

9. The therapy electrode system of claim 1, wherein the fluid pump is a peristaltic pump.

10. The therapy electrode system of claim 1, further comprising a sensor configured to provide an indication of whether the replaceable gel cartridge is intact.

11. The therapy electrode system of claim 10, wherein the sensor is a pressure sensor.

12. The therapy electrode system of claim 1, further comprising a sensor configured to provide an indication of whether the therapy electrode is properly inserted into the garment.

13. The therapy electrode system of claim 1, wherein the fluid pump provides a pressure of between about 10 psig and about 15 psig to the replaceable gel cartridge.

14. The therapy electrode system of claim 1, wherein the fluid pump provides a pressure of between about 15 psig and about 30 psig to the replaceable gel cartridge.

15. A therapy electrode system comprising:
a garment configured to be worn about a torso of a patient;
a therapy electrode disposed in the garment and configured to deliver one or more electrical shocks to a body of the patient;
a replaceable gel cartridge disposed on the therapy electrode and configured to release a conductive gel onto the patient's skin at an interface between the therapy electrode and the patient's skin prior to the delivery of the one or more electrical shocks to the body of the patient at the interface between the therapy electrode and the patient's skin;
a fluid pump in fluid communication with the replaceable gel cartridge; and
a sensor configured to provide an indication of whether the replaceable gel cartridge is intact.

16. The therapy electrode system of claim 15, wherein the sensor is a pressure sensor.

17. The therapy electrode system of claim 15, wherein the fluid pump is removably coupled to the replaceable gel cartridge.

18. A therapy electrode system comprising:
a garment configured to be worn about a torso of a patient;
a therapy electrode disposed in the garment and configured to deliver one or more electrical shocks to a body of the patient;
a replaceable gel cartridge disposed on the therapy electrode and configured to release a conductive gel onto the patient's skin at an interface between the therapy electrode and the patient's skin prior to the delivery of the one or more electrical shocks to the body of the patient at the interface between the therapy electrode and the patient's skin;
a fluid pump in fluid communication with the replaceable gel cartridge; and
a sensor configured to provide an indication of whether the therapy electrode is properly inserted into the garment.

19. The therapy electrode system of claim 18, wherein the fluid pump comprises an air pump.

20. The therapy electrode system of claim 18, comprising:
a plurality of therapy electrodes disposed in the garment; and
a monitor configured to monitor a physiological parameter of the patient utilizing the therapy electrode system.

* * * * *